(12) United States Patent
Hunt et al.

(10) Patent No.: US 7,449,027 B2
(45) Date of Patent: Nov. 11, 2008

(54) MODIFYING FLUID FLOW IN A BODY VESSEL LUMEN TO PROMOTE INTRALUMINAL FLOW-SENSITIVE PROCESSES

(75) Inventors: James B. Hunt, Bloomington, IN (US);
Brian C. Case, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 139 days.

(21) Appl. No.: 11/093,401

(22) Filed: Mar. 29, 2005

(65) Prior Publication Data
US 2005/0234541 A1 Oct. 20, 2005

Related U.S. Application Data

(60) Provisional application No. 60/557,219, filed on Mar. 29, 2004.

(51) Int. Cl.
*A61F 2/06* (2006.01)
(52) U.S. Cl. .................................. 623/1.24; 623/903
(58) Field of Classification Search ................ 623/1.24, 623/1.26, 2.2, 903, 904; 606/158, 159
See application file for complete search history.

(56) References Cited

U.S. PATENT DOCUMENTS

| | | |
|---|---|---|
| 4,178,639 A | 12/1979 | Bokros |
| 4,272,854 A | 6/1981 | Bokros |
| 4,276,658 A | 7/1981 | Hanson et al. |
| 4,328,592 A | 5/1982 | Klawitter |
| 4,363,142 A | 12/1982 | Meyer |
| 4,373,216 A | 2/1983 | Klawitter |
| 4,443,894 A | 4/1984 | Klawitter |
| 4,446,577 A | 5/1984 | Meyer et al. |
| 4,451,937 A | 6/1984 | Klawitter |

(Continued)

FOREIGN PATENT DOCUMENTS

EP 0 553 960 A1 1/1993

(Continued)

OTHER PUBLICATIONS

Badylak et al.; "Morphologic Study of Small Intestinal Submucosa as a Body Wall Repair Device;"*J. Surg. Research*, 103; pp. 190-202; 2002.

(Continued)

*Primary Examiner*—William (Howie) H Matthews
*Assistant Examiner*—Suba Ganesan
(74) *Attorney, Agent, or Firm*—Brinks Hofer Gilson & Lione

(57) ABSTRACT

The present invention, in one embodiment, provides an implantable intraluminal fluid flow control system comprising an interface and a flow-modifying device positioned at a flow-modifying effective distance from the interface within the lumen of a body vessel. In one embodiment, the invention relates to maintaining, regulating or varying the fluid flow within a body vessel to preserve, promote, alter or enhance remodeling of tissue at the interface. Remodeling can include the resorption and replacement of implanted remodelable material with autologous tissue. The interface can comprise remodelable material such as small intestine submucosa. In one embodiment, one or more interfaces are positioned at flow-modifying effective distances from one or more flow-modifying devices. Related medical devices, kits and methods of treatment are also provided in some embodiments.

13 Claims, 6 Drawing Sheets

U.S. PATENT DOCUMENTS

| | | | |
|---|---|---|---|
| 4,605,408 | A | 8/1986 | Carpentier |
| 4,676,789 | A | 6/1987 | Sorensen et al. |
| 4,692,165 | A | 9/1987 | Bokros |
| 4,822,353 | A | 4/1989 | Bokros |
| 4,863,458 | A | 9/1989 | Bokros |
| 4,863,459 | A | 9/1989 | Olin |
| 4,872,875 | A | 10/1989 | Hwang |
| 4,888,010 | A | 12/1989 | Bokros |
| 4,892,540 | A | 1/1990 | Vallana |
| 4,902,508 | A | 2/1990 | Badylak et al. |
| 4,923,465 | A | 5/1990 | Knoch et al. |
| 4,935,030 | A | 6/1990 | Alonso |
| 4,950,227 | A | 8/1990 | Savin et al. |
| 4,956,178 | A | 9/1990 | Badylak et al. |
| 4,995,881 | A | 2/1991 | Knoch et al. |
| 5,002,567 | A | 3/1991 | Bona et al. |
| 5,061,278 | A | 10/1991 | Bicer |
| 5,078,738 | A | 1/1992 | Couetil |
| 5,108,416 | A | 4/1992 | Ryan et al. |
| 5,108,425 | A | 4/1992 | Hwang |
| 5,116,366 | A | 5/1992 | Hwang |
| 5,116,367 | A | 5/1992 | Hwang et al. |
| 5,123,920 | A | 6/1992 | Bokros |
| 5,137,532 | A | 8/1992 | Bokros et al. |
| 5,147,390 | A | 9/1992 | Campbell |
| 5,152,785 | A | 10/1992 | Bokros et al. |
| 5,171,263 | A | 12/1992 | Boyer et al. |
| 5,178,632 | A | 1/1993 | Hanson |
| 5,192,309 | A | 3/1993 | Stupka et al. |
| 5,192,313 | A | 3/1993 | Budd et al. |
| 5,197,980 | A | 3/1993 | Gorshkov et al. |
| 5,222,970 | A | 6/1993 | Reeves |
| 5,250,038 | A | 10/1993 | Melker et al. |
| 5,275,826 | A | 1/1994 | Badylak et al. |
| 5,281,422 | A | 1/1994 | Badylak et al. |
| 5,334,210 | A | 8/1994 | Gianturco |
| 5,403,341 | A | 4/1995 | Solar |
| 5,409,495 | A | 4/1995 | Osborn |
| 5,554,389 | A | 9/1996 | Badylak et al. |
| 5,643,317 | A | 7/1997 | Pavcnik et al. |
| 5,668,288 | A | 9/1997 | Storey et al. |
| 5,733,337 | A | 3/1998 | Carr, Jr. et al. |
| 5,769,887 | A | 6/1998 | Brown et al. |
| 5,976,153 | A | 11/1999 | Fischell et al. |
| 5,993,844 | A | 11/1999 | Abraham et al. |
| 6,045,557 | A | 4/2000 | White et al. |
| 6,099,567 | A | 8/2000 | Badylak et al. |
| 6,126,686 | A | 10/2000 | Badylak et al. |
| 6,171,338 | B1 | 1/2001 | Talja et al. |
| 6,206,931 | B1 | 3/2001 | Cook et al. |
| 6,334,872 | B1 | 1/2002 | Termin et al. |
| 6,346,118 | B1 | 2/2002 | Baker et al. |
| 6,375,989 | B1 | 4/2002 | Badylak et al. |
| 6,395,017 | B1 | 5/2002 | Dwyer et al. |
| 6,419,685 | B2 | 7/2002 | Di Caprio et al. |
| 6,444,229 | B2 | 9/2002 | Voytik-Harbin et al. |
| 6,508,833 | B2 | 1/2003 | Pavcnik et al. |
| 6,544,268 | B1 | 4/2003 | Lazarus |
| 6,562,068 | B2 | 5/2003 | Drasler et al. |
| 6,572,650 | B1 | 6/2003 | Abraham et al. |
| 6,579,538 | B1 | 6/2003 | Spievack |
| 6,582,394 | B1 | 6/2003 | Reiss et al. |
| 6,602,286 | B2 | 8/2003 | Strecker |
| 6,607,555 | B2 | 8/2003 | Patterson et al. |
| 2001/0039450 | A1 | 11/2001 | Pavcnik et al. |
| 2002/0099439 | A1* | 7/2002 | Schwartz et al. ........... 623/1.24 |
| 2003/0144670 | A1 | 7/2003 | Pavcnik et al. |
| 2004/0137042 | A1 | 7/2004 | Hiles et al. |
| 2004/0180042 | A1 | 9/2004 | Cook et al. |
| 2004/0236346 | A1 | 11/2004 | Parker |

FOREIGN PATENT DOCUMENTS

| | | |
|---|---|---|
| EP | 0 553 960 B1 | 1/1993 |
| EP | 0 657 147 A2 | 6/1995 |
| EP | 0 657 147 A3 | 6/1995 |
| EP | 0 657 147 B1 | 6/1995 |
| EP | 0 701 800 A1 | 3/1996 |
| EP | 0 701 800 B1 | 3/1996 |
| WO | WO 98/22158 A2 | 5/1998 |
| WO | WO 98/25636 A1 | 6/1998 |
| WO | WO 98/25637 A1 | 6/1998 |
| WO | WO98/26291 A1 | 6/1998 |

OTHER PUBLICATIONS

Bain, William H. et al.; "Tilting Disc Valves;" *Replacement Cardiac Valves*; Eds. Endre Bodnar and Robert Frater; New York; Pergamon Press; pp. 187-200; 1991.

Brountzos et al.; "Remodeling of suspended small intestinal submucosa venous valve: an experimental study in sheep to assess the host cells' origin;" *J. Vasc. Interv. Radiol.*, 14; pp. 349-356; 2003.

DeWall, M.D. et al.; "Evolution of Mechanical Heart Valves," *Ann. Thorac. Surg.*; 69; pp. 1612-1621; 2000.

Fann, James I. et al.; "Caged-Ball Valves: The Starr-Edwards and Smeloff-Sufter Prostheses;" *Replacement Cardiac Valves*; Eds. Endre Bodnar and Robert Frater; New York; Pergamon Press; pp. 149-186; 1991.

Harmon, Jr. et al.; "Venous valves in subclavian and internal jugular veins: frequency, position and structure in 100 autopsy cases;" *Am J Cardiovasc Pathol*; 1(1): pp. 51-54; Jan. 1987.

Horstkotte, Dieter et al.; "Bileaflet Valves," *Replacement Cardiac Valves*; Eds. Endre Bodnar and Robert Frater; New York; Pergamon Press; pp. 201-228; 1991.

Iimura, Akira et al.; "Anatomical Study of distribution of valves of the cutaneous veins of adult's limbs;" *Ann. Anat* 185; 91-95; 2003.

Kim et al.; "Small intestinal submucosa as a small-caliber venous graft: a novel model for hepatocyte transplantation on synthetic biodegradable polymer scaffolds with direct access to the portal venous system;" *J. Pediatr. Surg.*; 34(1); pp. 124-128; Jan. 1999.

Lefrak, M.D., Edward A. and Albert Starr, M.D., Eds.; *Cardiac Valve Prostheses*; New York; Appleton-Century-Crofts; pp. 1-37.

McGoon, D. C.; "The Status of Prosthetic Cardiac Valves;" *Biological Tissue in Heart Valve Replacement*; Eds. M. I. Ionescu, D. N. Ross, and G. H. Wooler; London; Butterworths; pp. 3-19.

Pavcnik, M.D. et al.; "Percutaneous bioprosthetic venous valve: A long-term study in sheep;" J. Vasc. Surg.; 35; pp. 598-603; 2002.

Phillips, M.N., et al.; "Micro-venous valves in the superficial veins of the human lower limb," *Clin. Anat.*; 17(1); pp. 55-60; 2004.

Roeder et al.; "Mechanical remodeling of small-intestine submucosa small-diameter vascular grafts—a preliminary report;" *Biomed. Instrum. Technol.*; 35(2); pp. 110-120; Mar. 2001.

Sandusky et al.; "Histologic findings after in vivo placement of small intestine submucosal vascular grafts and saphenous vein grafts in carotid artery in dogs;" *Am. J. Pathol.*; 140(2); pp. 317-324; Feb. 1992.

Santilli, M.D., S.M. et al.; "Superficial femoral popliteal vein: An anatomic study;" *J Vasc Surg*; 31(3); pp. 450-455; 2000.

Sum-Ping et al.; "Internal Jugular Valves: Competent or Incompetent?;" Anesth. Analg.; 78; pp. 1039-1040; 1994.

* cited by examiner

MODIFYING FLUID FLOW IN A BODY VESSEL LUMEN TO PROMOTE INTRALUMINAL FLOW-SENSITIVE PROCESSES

This application claims the benefit of U.S. Provisional Application No. 60/557,219, filed Mar. 29, 2004, entitled, "Modifying Fluid Flow in a Body Vessel Lumen to Promote Intraluminal Flow-Sensitive Processes," which is incorporated herein by reference in its entirety.

FIELD OF THE INVENTION

The present invention relates to the promotion of flow-sensitive processes occurring on medical devices implanted in the lumen of a body vessel. The invention also relates to intraluminal fluid flow control systems, medical devices, kits and methods for the promotion of flow-sensitive processes at one or more implantable interface(s).

BACKGROUND

Many vessels in animals transport fluids from one bodily location to another. In some vessels, such as mammalian veins, natural valves are positioned along the length of the vessel to permit fluid flow in a substantially unidirectional manner along the length of the vessel. While natural valves may function for an extended time, some may lose effectiveness, which can lead to physical manifestations and clinical indications. Natural venous valves are susceptible to becoming insufficient following damage to valve leaflets and resulting formation of thrombus or scar tissue, compromising the ability of the valve leaflets to close properly. Once natural venous valves are damaged, venous valve insufficiency can occur, which can lead to various clinical indications such as discomfort and ulcers in the legs and ankles.

Minimally invasive techniques and instruments for placement of intraluminal medical devices have been developed to treat and repair such undesirable conditions within bodily vessels, including treatment of venous valve insufficiency. For example, intraluminal medical devices can be deployed in a vessel at a point of treatment, the delivery device withdrawn from the vessel, and the medical device retained within the vessel to provide sustained improvement in vascular valve function.

For treatment of many conditions, it is desirable that implantable medical devices comprise remodelable material. Implanted remodelable material provides a matrix or support for the growth of new tissue thereon, and remodelable material is resorbed into the body in which the device is implanted. Common events during this remodeling process include: widespread neovascularization, proliferation of granulation mesenchymal cells, biodegradation/resorption of implanted remodelable material, and absence of immune rejection. By this process, autologous cells from the body can replace the remodelable portions of the medical device.

A variety of remodelable materials are available for use in implantable medical devices. Naturally derived or synthetic collagenous materials can be used to provide remodelable surfaces on implantable medical devices. Naturally derived or synthetic collagenous material, such as extracellular matrix material, are another category of remodelable materials that include, for instance, submucosa, renal capsule membrane, dura mater, pericardium, serosa, and peritoneum or basement membrane materials. One specific example of an extracellular matrix material is small intestine submucosa (SIS). When implanted, SIS can undergo remodeling and can induce the growth of endogenous tissues upon implantation into a host. SIS has been used successfully in vascular grafts, urinary bladder and hernia repair, replacement and repair of tendons and ligaments, and dermal grafts.

Once implanted, however, remodelable material is often subjected to dynamic fluid flow. Changes in the flow rate, flow direction or fluid pressure of intraluminal fluid across an implanted remodelable material has the potential to disrupt or slow the remodeling process. The intraluminal fluid flow can be characterized by parameters such as pressure, direction, composition and flow rate across the interface. Intraluminal fluid flow in a vascular environment is subject to regular modulations in pressure and fluid flow between diastole and systole pressures. The remodeling process itself may be linked to the flow of fluid across the remodelable surface. Recent investigations have shown that SIS-based remodeling of implanted medical devices can occur by recruitment of cells directly from intraluminal circulation. See Brountzos, et al, "Remodeling of suspended small intestinal submucosa venous valve: an experimental study in sheep to assess the host cells' origin," *J. Vasc. Interv. Radiol.*, 14(3), 349-356 (March 2003).

Remodelable material implanted within a fluid-containing body vessel forms an interface between the remodelable material and the fluid within the body vessel that is contacting the remodelable material. The interface is potentially sensitive to, or responsive to, the flow of intraluminal fluid across the interface.

It is desirable to have systems, methods and kits relating to the implantation of medical devices in a body vessel that regulate fluid flow in the body vessel as taught herein, for example to promote the remodeling of tissue at an interface.

SUMMARY

In one embodiment, an implantable intraluminal fluid flow control system according to the invention comprises an interface separated from a flow-modifying device by a distance effective to modify fluid flow at the interface within the lumen of a body cavity, such as a body vessel. The interface is sensitive to or responsive to fluid flow across its surface. In another embodiment, the implantable intraluminal fluid flow control system comprises an interface and a means for modifying fluid flow in the lumen of a body vessel, where the means for modifying fluid flow can be positioned at a flow-modifying effective distance from the interface. In one embodiment, a flow-modifying device substantially occludes fluid flow along one or more portions of a branched body vessel, thereby diverting fluid flow to other branches of the body vessel. In some embodiments, the interface and the flow-modifying device form separate components. In one embodiment, the interface and the flow-modifying device can be operatively connected in a single medical device. The intraluminal fluid flow control system of the invention can further comprise a means for delivering the single implantable medical device to the lumen of a body vessel.

In some embodiments, the interface comprises a remodelable material. For example, the interface can comprise an extracellular matrix material, such as small intestine submucosa (SIS). In one embodiment, the interface is a valve device. For example, the interface can be a valve comprising SIS material, such as an implanted venous valve.

In some embodiments, the flow-modifying device is a mechanical valve. For example, the mechanical valve can be selected from the group consisting of: a caged ball valve, a central flow valve, a tilting disc valve, a non-tilting disc valve, and a bileaflet valve. In one embodiment, the flow-modifying device comprises a mechanical valve that is adapted to allow fluid to flow through the valve upon failure of the valve, for example by applying a mechanical bias to the valve. In other embodiments, the flow-modifying device substantially occludes fluid flow in a body vessel, for example to divert fluid flow to other branches of a branched body vessel network.

In some embodiments, an implantable intraluminal fluid flow control system according to the invention comprises one or more interface(s) and one or more flow-modifying device(s), such each interface is separated from a flow-modifying device by a distance effective to modify fluid flow at the interface within the lumen of a body cavity, such as a body vessel. Multiple interfaces or multiple flow-modifying devices can be employed in certain embodiments of the invention. The combination of multiple interfaces or flow-modifying devices can be positioned within the lumen of a body cavity so as to not substantially hinder or prevent the preservation, promotion, or enhancement of a desired process at an implanted interface. Accordingly, in one embodiment, the invention provides a first interface positioned at a first distance within a body cavity and effective to modify flow at a flow-modifying device, a second interface positioned at a second distance within the body cavity and effective to modify flow at the second interface, such that the second interface is in cooperative fluid flow communication with the first interface.

Kits are also provided. In some embodiments, a kit comprises an implantable interface and an implantable flow-modifying device. The implantable interface can comprise a remodelable material. The implantable interface can be, for example, an implantable venous valve comprising SIS. In some embodiments, the kit comprises an interface and the flow-modifying device that are operatively connected in a single implantable medical device. In one embodiment, a kit comprises a means for delivering the interface, the implantable medical device, the flow-modifying device, or any combination thereof, to the lumen of a body vessel. For example, the kit can comprise a flow-modifying device that is a mechanical valve.

The invention also provides methods of modifying intraluminal fluid flow at an interface. In one embodiment, the invention comprises deploying a flow-modifying device within a body cavity separated from an interface by a distance from the interface that is effective to modify fluid flow at the interface and within a body cavity. In one embodiment, the invention comprises deploying an interface at a distance from a flow-modifying device that is effective to modify the flow at the interface. In one embodiment, the method employs an interface that is a venous valve comprising SIS. In one embodiment, fluid flow is modified by diverting fluid flow to other body vessels, for example by implanting a flow-modifying device that substantially prevents fluid flow along a segment of a branched network of veins.

The invention also provides methods of treatment. One method according to the invention comprises the acts of: delivering the first interface to a first point of treatment, delivering a flow-modifying device, such as a mechanical valve, to a second point of treatment separated from the first point of treatment within the lumen of a body cavity by a distance that is effective to modify fluid flow at the interface. In one embodiment, the first interface and the first flow-modifying device are operatively connected in a single implantable medical device, and the first point of treatment and the second point are substantially adjacent to one another within the lumen of a body cavity, such as a body vessel. In one embodiment, methods are provided that employ multiple interfaces or multiple flow-modifying devices. In one embodiment, the invention provides a method of treating a patient further comprising (in any order) the acts of: delivering a second interface to a third point of treatment spaced from the second point of treatment by a distance effective to modify flow at the second interface. The second interface can be delivered to a point in cooperative fluid flow communication with the first interface. In one embodiment, the method employs one or more interfaces that comprise SIS. In another embodiment, a flow-modifying device is implanted to temporarily reduce, or substantially prevent, fluid flow along a portion of a body vessel comprising a remodelable material. For example, a flow-modifying device can be implanted to substantially occlude fluid flow along a portion of a branched network of veins that contains an incompetent venous valve.

DETAILED DESCRIPTION OF EMBODIMENTS

Figure 1A:
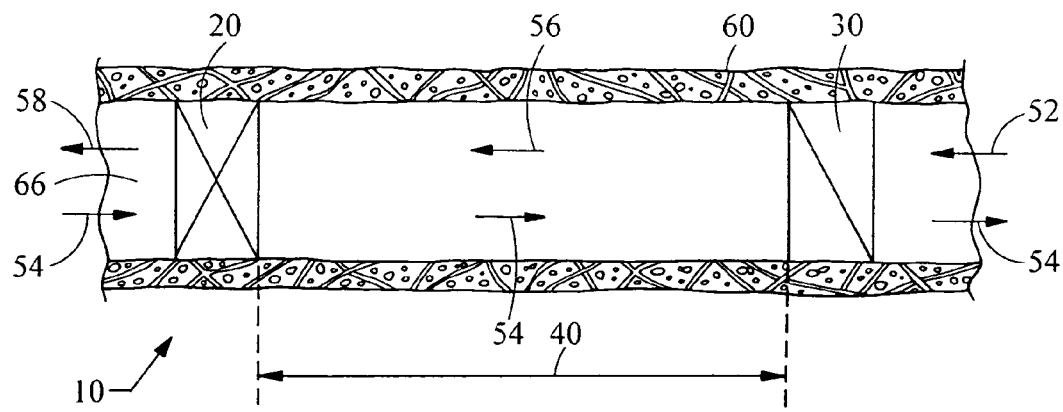
FIG. 1A, FIG. 1B and FIG. 1C provide schematic views of certain embodiments demonstrating various configurations of an interface and a flow-modifying device within a body vessel.

In one embodiment, the present invention relates to regulating fluid flow across implanted medical devices within a body vessel. In one embodiment, the fluid flow regulation can promote the resorption and replacement of implanted material with autologous tissue. In another embodiment, the invention also relates to kits and methods for such fluid flow regulation.

For the purposes of promoting an understanding of the principles of the invention, the following provides a detailed description of some embodiments of the invention as illustrated by the drawings. The description is not intended to limit the invention in any manner, but rather serves to enable those skilled in the art to make and use the invention. As used herein the terms "comprise(s)," "include(s)," "having," "has," "contain(s)," and variants thereof, are intended to be open-ended transitional phrases, terms, or words that do not preclude the possibility of additional acts or structure.

"Fluid flow" refers to the stream-like movement of a fluid within the lumen of a body vessel. "Flow-modifying," "effective to modify fluid flow," or "fluid flow-modifying" refer to either: (1) maintaining, regulating or varying the rate of fluid flow across, or in contact with, an interface, or (2) maintaining, regulating or varying the composition of the fluid flowing across, or in contact with, an interface.

As used herein, an "interface" refers to an implantable device or material comprising at least one surface that contacts fluid within a body vessel upon implantation of the interface within the body vessel without a flow-modifying device. A flow-modifying device can modify or prevent fluid contact with the implanted interface. Preferably, after implantation, the material of the interface surface contacting the fluid within the body vessel undergoes a desirable process that is affected by fluid contacting the implanted material. A "desirable process" is a process that is commensurate with goals for treatment of a subject. Examples of a desirable process at the interface are the deposition or growth of cells on the surface of the interface, or the resorption or dissolution of the material of the interface. An endoluminally implantable valve comprising leaflets made from a remodelable material is one example of an interface. A "venous valve interface" is an interface is a valve adapted for implantation within a vein.

As used herein, the term "body vessel" means any tube-shaped body passage lumen that conducts fluid, including but not limited to blood vessels such as those of the human vasculature system, billiary ducts and ureteral passages.

As used herein, the term "implantable" refers to an ability of a structure (e.g., an interface or a flow-modifying device) to be positioned at a location within body, such as within a body vessel. Furthermore, the terms "implantation," and "implanted," refer to the positioning of a structure at a location within a body, such as within a body vessel.

As used herein, "endolumenally," "intraluminally" or "transluminal" all refer synonymously to implantation placement by procedures wherein the prosthesis is advanced within and through the lumen of a body vessel from a remote location to a target site within the body vessel. In vascular procedures, a medical device will typically be introduced "endovascularly" using a catheter over a guidewire under fluoroscopic guidance. The catheters and guidewires may be introduced through conventional access sites to the vascular system, such as through the femoral artery, or brachial and subclavian arteries, for access to the coronary arteries.

As used herein, "bioabsorbable polymer" refers to a polymer or copolymer which is absorbed by the body.

A "biocompatible" material is a material that is compatible with living tissue or a living system by not being toxic or injurious and not causing immunological rejection.

"Non-bioabsorbable" material refers to a material, such as a polymer or copolymer, which remains in the body without substantial bioabsorption.

Intraluminal Fluid Control Systems

Figure 1B:
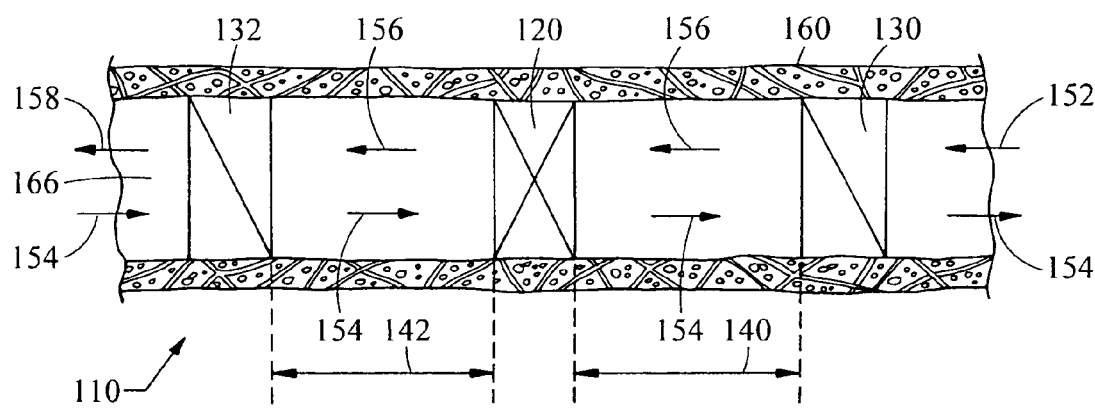
Figure 1C:
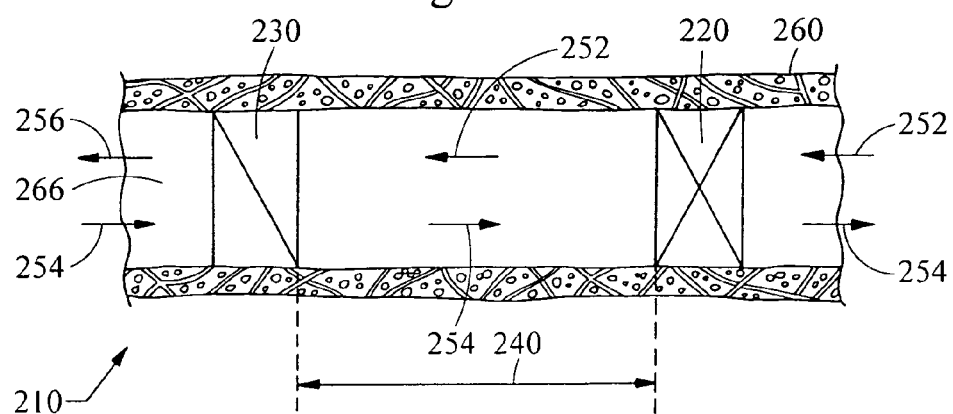

As shown schematically in FIG. 1A, FIG. 1B, and FIG. 1C, a fluid control system of some embodiments of the present invention comprises an interface and a flow-modifying device that is positioned at a flow-modifying effective distance with respect to the interface. Placement of one or more fluid flow-modifying devices with respect to interface is shown schematically in FIG. 1A, FIG. 1B, and FIG. 1C, however any suitable device or material can be used to perform the flow-modifying function or the interface function.

FIG. 1A illustrates an intraluminal fluid flow control system 10, wherein an interface 20 and a flow-modifying device 30 are individually deployed within a lumen 56 defined by a body vessel 60. The lumen 66 provides a conduit for fluid flow through the body vessel 60. A primary fluid flow 52 is primarily directed in a downstream direction, but can be permitted to flow in an opposite, retrograde direction (retrograde flow 54). In FIG. 1A, the interface 20 is positioned at a flow-modifying effective distance 40 in the downstream direction from the flow-modifying device 30. Primary fluid flow 52 is modified by passing through the flow-modifying device 30, so that a modified fluid flow 56 contacts the interface 20. One example of a flow-modifying device 30 is an implantable ring that reduces the rate of the modified fluid flow 56 compared to the rate of primary fluid flow 52. The flow-modifying device 30 can also be a bioabsorbable occluding device that substantially blocks primary fluid flow 52 and retrograde flow 54, so that the modified fluid flow 56 is negligible. After implantation, the bioabsorbable occluding device is reabsorbed by the body, thereby restoring a modified fluid flow 56 that is similar to the primary fluid flow 52 present in the body vessel 60 without the flow-modifying device 30.

FIG. 1B illustrates an intraluminal fluid flow control system 110, wherein an interface 120, a first flow-modifying device 130 and a second flow-modifying device 132 are positioned within a lumen 166 defined by a body vessel 160. The interface 120 is positioned between two flow-modifying devices, at a first flow-modifying effective distance 140 in the downstream direction from the first flow-modifying device 130 and at a second flow-modifying effective distance 142 in the retrograde direction from the second flow-modifying device 132. As in FIG. 1A, a primary fluid flow 152 is modified by the first flow-modifying device 130, so the interface 120 is subject to a modified fluid flow 156 in the downstream direction. The interface 120 can also be exposed to retrograde fluid flow 154 in the opposite (retrograde) direction, which is optionally modified by the second flow-modifying device 132. In FIG. 1B, the modified fluid flow 156 is modified by the second flow-modifying device 132 to provide a second modified fluid flow 158.

FIG. 1C illustrates an intraluminal fluid flow control system 210, where an interface 220 is positioned at a flow-modifying effective distance 240 in the retrograde direction from the flow-modifying device 230 within the lumen 266 of a body vessel 260. In a vein, the interface 230 and the flow-modifying device 230 are also subject to a retrograde flow 254 between pulses of the primary fluid flow 252. The flow-modifying device 230 acts to modify the primary fluid flow 252 to a modified fluid flow 256, after the primary fluid flow 252 contacts the interface 220.

Other arrangements of interface structures and flow-modifying device structures are contemplated within the scope of the invention. Other embodiments of the invention include positioning one or more interface structures each at a flow-modifying effective distance from one or more flow-modifying device structures. In some embodiments, such as those illustrated in FIG. 1A, FIG. 1B and FIG. 1C, the flow-modifying device is positioned within the lumen defined by a body vessel.

Interfaces

By locating the interface near a flow-modifying device, the affect of fluid flow on the interface can be modulated. In one embodiment, the interface can be an implantable medical device comprising remodelable material. For example, in one embodiment, the interface is an implantable venous valve comprising SIS material positioned to be in contact with bodily fluid upon implantation. In another embodiment, the interface can be the portion of an implantable device comprising implantable material that is responsive to fluid contacting the implantable material. In another embodiment, fluid can permeate or selectively permeate pores in sheet material, or in perforated sheet material. One embodiment provides an interface comprising cellular material having a repeating array of three-dimensional cavities within an implantable material such that the interface comprises the surface area portion of the pores or cells within the material that is responsive to the fluid contacting the pore surface.

Interface Materials

A variety of materials are available for providing an interface. One skilled in the art will appreciate that various materials can be used to provide an interface that can be implanted.

In one embodiment, the interface can comprise a substantially biocompatible material, such as polyester fabrics, polytetrafluoroethylene (PTFE), expanded PTFE, and other synthetic materials known to those of skill in the art. In one embodiment, the interface can comprise a naturally occurring biomaterial, such as collagen. In one embodiment, the interface comprises a collagen material known as extracellular matrix (ECM). In one embodiment, a suitable ECM is small intestinal submucosa (SIS). Other examples of ECMs are pericardium, stomach submucosa, liver basement membrane, urinary bladder submucosa, tissue mucosa, and dura mater.

In one embodiment, the interface can comprise a remodelable material. The terms "remodelable" or "bioremodelable" refer to the ability of a material to allow or induce host tissue growth, proliferation or regeneration following implantation of the tissue in vivo. Remodeling can occur in various microenvironments within a body, including without limitation soft tissue, a sphincter muscle region, body wall, tendon, ligament, bone and cardiovascular tissues. Upon implantation of a remodelable material, cellular infiltration and neovascularization are typically observed over a period of about five days to about six months or longer, as the remodelable material acts as a matrix for the ingrowth of adjacent tissue with site-specific structural and functional properties. The remodeling phenomenon which occurs in mammals following implantation of submucosal tissue includes rapid neovascularization and early mononuclear cell accumulation. Mesenchymal and epithelial cell proliferation and differentiation are typically observed by one week after in vivo implantation and extensive deposition of new extracellular matrix occurs almost immediately. In some embodiments, fluid contacting autologous cells on an implanted remodelable material interface can affect the growth of autologous tissue on the implanted remodelable material.

One example of a suitable remodelable material useful as an interface is extracellular matrix (ECM) material derived from submocosal tissue. Submucosal tissue can be obtained from various tissue sources, harvested from animals raised for meat production, including, for example, pigs, cattle and sheep or other mammals. More particularly, the submucosa is isolated from warm-blooded tissues including the alimentary, respiratory, intestinal, urinary or genital tracts of warm-blooded vertebrates.

One preferred category of ECM material is submucosal tissue. Submucosal ECM material can be obtained from any suitable source, including without limitation, intestinal submucosa, stomach submucosa, urinary bladder submucosa, and uterine submucosa. Intestinal submucosal tissue is one preferred starting material, and more particularly intestinal submucosa delaminated from both the tunica muscularis and at least the tunica mucosa of warm-blooded vertebrate intestine. More preferably, the ECM material is Tela submucosa, which is a layer of collagen-containing connective tissue occurring under the mucosa in most parts of the alimentary, respiratory, urinary and genital tracts of animals. Examples of suitable ECM materials include renal capsule matrix (RCM), urinary bladder matrix (UBM) and most preferably small intestine submucosa (SIS). Most preferably, the ECM material is obtained from processed intestinal collagen layer derived from the tunic submucosa of porcine small intestine.

"Tela submucosa" refers to a layer of collagen-containing connective tissue occurring under the mucosa in most parts of the alimentary, respiratory, urinary, integumentary, and genital tracts of animals. Tela submucosa, as with many animal tissues, is generally aseptic in its natural state, provided the human or animal does not have an infection or disease. This is particularly the case since the tela submucosa is an internal layer within the alimentary, respiratory, urinary and genital tracts of animals. Accordingly, it is generally not exposed to bacteria and other cellular debris such as the epithelium of the intestinal tract. Preferably, the tela submucosa tissue ECM materials, which are collagen-based and thus predominantly collagen, are derived from the alimentary tract of mammals and most preferably from the intestinal tract of pigs. A most preferred source of whole small intestine is harvested from mature adult pigs weighing greater than about 450 pounds. Intestines harvested from healthy, nondiseased animals will contain blood vessels and blood supply within the intestinal tract, as well as various microbes such as $E.$ $coli$ contained within the lumen of the intestines. Therefore, disinfecting the whole intestine prior to delamination of the tela submucosa substantially removes these contaminants and provides a preferred implantable tela submucosa tissue which is substantially free of blood and blood components as well as any other microbial organisms, pyrogens or other pathogens that may be present. In effect, this procedure is believed to substantially preserve the inherent aseptic state of the tela submucosa, although it should be understood that it is not intended that the present invention be limited by any theory.

Additional information as to submucosa materials useful as ECM materials herein can be found in U.S. Pat. Nos. 4,902,508; 5,554,389; 5,993,844; 6,206,931; 6,099,567; and 6,375,989, as well as published U.S. Patent Applications US2004/0180042A1 and US2004/0137042A1, which are all incorporated herein by reference. For example, the mucosa can also be derived from vertebrate liver tissue as described in WIPO Publication, WO 98/25637, based on PCT application PCT/US97/22727; from gastric mucosa as described in WIPO Publication, WO 98/26291, based on PCT application PCT/US97/22729; from stomach mucosa as described in WIPO Publication, WO 98/25636, based on PCT application PCT/US97/23010; or from urinary bladder mucosa as described in U.S. Pat. No. 5,554,389; the disclosures of all are expressly incorporated herein.

An interface can comprise an ECM material isolated from biological tissue by a variety of methods. In general, an ECM material can be obtained from a segment of intestine that is first subjected to abrasion using a longitudinal wiping motion to remove both the outer layers (particularly the tunica serosa and the tunica muscularis) and the inner layers (the luminal portions of the tunica mucosa). Typically the SIS is rinsed with saline and optionally stored in a hydrated or dehydrated state until use as described below. The resulting submucosa tissue typically has a thickness of about 100-200 micrometers, and may consist primarily (greater than 98%) of acellular, eosinophilic staining (H&E stain) ECM material.

Perferably, the source tissue for the ECM material is a tela submucosa that is disinfected prior to delamination by the preparation disclosed in US Patent Application US2004/0180042A1 by Cook et al., published Sep. 16, 2004 and incorporated herein by reference in its entirety. Most preferably, the tunica submucosa of porcine small intestine is processed in this manner to obtain the ECM material. This method is believed to substantially preserve the aseptic state of the tela submucosa layer, particularly if the delamination process occurs under sterile conditions. Specifically, disinfecting the tela submucosa source, followed by removal of a purified matrix including the tela submucosa, e.g. by delaminating the tela submucosa from the tunica muscularis and the tunica mucosa, minimizes the exposure of the tela submucosa to bacteria and other contaminants. In turn, this enables minimizing exposure of the isolated tela submucosa matrix to disinfectants or sterilants if desired, thus substantially preserving the inherent biochemistry of the tela submucosa and many of the tela submucosa's beneficial effects.

Preferably, the ECM material is substantially free of any antibiotics, antiviral agents or any antimicrobial type agents which may affect the inherent biochemistry of the matrix and its efficacy upon implantation. An alternative to the preferred method of ECM material isolation comprises rinsing the delaminated biological tissue in saline and soaking it in an antimicrobial agent, for example as disclosed in U.S. Pat. No. 4,956,178. While such techniques can optionally be practiced to isolate ECM material from submucosa, preferred processes avoid the use of antimicrobial agents and the like which may not only affect the biochemistry of the collagen matrix but also can be unnecessarily introduced into the tissues of the patient.

Other disclosures of methods for the isolation of ECM materials include the preparation of intestinal submucosa described in U.S. Pat. No. 4,902,508, the disclosure of which is incorporated herein by reference. Urinary bladder submucosa and its preparation is described in U.S. Pat. No. 5,554,389, the disclosure of which is incorporated herein by reference. Stomach submucosa has also been obtained and characterized using similar tissue processing techniques, for example as described in U.S. patent application Ser. No. 60/032,683 titled STOMACH SUBMUCOSA DERIVED TISSUE GRAFT, filed on Dec. 10, 1996, which is also incorporated herein by reference in its entirety.

In some embodiments, submucosal tissues for use in accordance with this invention include intestinal submucosa, stomach submucosa, urinary bladder submucosa, and uterine submucosa. Another specific example of a suitable remodelable material is intestinal submucosal tissue, and more particularly intestinal submucosa delaminated from both the tunica muscularis and at least the tunica mucosa of warm-blooded vertebrate intestine.

SIS can be made, for example, in the fashion described in U.S. Pat. No. 4,902,508 to Badylak et al., U.S. Pat. No. 5,733,337 to Carr, and WIPO Patent No. WO 9822158, published May 28, 1998, issued to Cook Biotech Inc. et al. and listing Patel et al. as inventors. The preparation and use of SIS is also described in U.S. Pat. Nos. 5,281,422 and 5,275,826. Urinary bladder submucosa and its preparation is described in U.S. Pat. No. 5,554,389, the disclosure of which is expressly incorporated herein by reference. The use of submucosal tissue in sheet form and fluidized forms for inducing the formation of endogenous tissues is described and claimed in U.S. Pat. Nos. 5,281,422 and 5,275,826, the disclosures of which are expressly incorporated herein by reference.

A variety of remodelable materials are known in the art, including naturally derived or synthetic collagenous materials that are capable of providing remodelable surfaces on implantable medical devices. Examples of interface materials useful in certain embodiments of the present invention also include: the regenerative compositions comprising epithelial basement membranes as described in U.S. Pat. No. 6,579,538 to Spievack, the remodelable implantable valves described in U.S. Pat. No. 6,126,686 to Badylak et al., the enzymatically digested submucosal gel matrix composition of U.S. Pat. No. 6,444,229 to Voytik-Harbin et al., materials comprising the carboxy-terminated polyester ionomers described in U.S. Pat. No. 5,668,288 to Storey et al., the biodegradable surgical implant of U.S. Pat. No. 6,171,338 to Talja et al., collagen-based matrix structure described in U.S. Pat. No. 6,334,872 to Termin et al., the autologous tissue venous valve described in U.S. Pat. No. 6,562,068 to Drasler et al., and combinations thereof.

Although certain embodiments of the present invention provide an interface comprising remodelable material, the invention is not limited to interface materials that are remodelable. Any material known in the art that provides a desirable property that is responsive to fluid contacting the surface when implanted in vivo can be used to provide an interface.

Any suitable implantable material or portion of an implantable material, including those described above, can serve as the interface. The examples recited above provide illustrative examples of some suitable materials that can be selected to provide an interface. Other materials known in the art can also be selected to provide an interface for some embodiments of the present invention.

Implantable Medical Devices Comprising an Interface

In one embodiment, the interface can be an implantable medical device comprising a remodelable material or a suitable biocompatible polymer. For example, in one embodiment, the interface is an implantable venous valve comprising SIS material positioned to be in contact with bodily fluid upon implantation. In one embodiment, the interface can be a portion of an implantable device that can be affected by fluid contacting the implantable material, including portions of the surface of the implantable device where desirable processes occur. In one embodiment, fluid can permeate pores in an implantable material such that the fluid contacting the pore surface can affect one or more desirable processes at the interface.

In one embodiment, the interface forms at least a portion of an implantable medical device. In one embodiment, the invention provides an implantable venous valve comprising one or more leaflets interfaces. An implantable venous valve can comprise one or more flexible leaflets made from SIS material that undergo remodeling upon implantation in a vein. Examples of suitable implantable venous valves include those described in U.S. Pat. No. 6,508,833 to Pavcnik et al, published U.S. Patent Application 2001, 0039450 to Pavcnik, and U.S. Provisional Patent Application Ser. No. 60/459,475, filed Apr. 1, 2003. Other types of suitable venous valves and other medical devices are known in the art and can also be used to provide an interface in accordance with some embodiments of the present invention.

Flow-Modifying Devices

As used herein, the term "flow-modifying device" means any device that can alter, maintain, regulate or vary the fluid flow contacting an interface, preferably in a manner that preserves, promotes, alters, or enhances a desired process at the interface. In certain preferred embodiments, a flow-modifying device substantially prevents fluid flow from contacting an interface within a body vessel. A desired process at the interface can be, for example, that of autologous tissue remodeling, including the growth of cells on the surface of the interface, upon implantation of the interface. The desired process at the interface can also be the resorption of the material of the interface material after implantation. For example, the desired process can be maintaining and preserving the in vivo functionality of an implanted valve, such as a venous valve.

In a preferred embodiment, the flow-modifying device substantially reduces or occludes fluid flow contacting the interface within a body vessel for a period of time effective to promote remodeling of a portion of the interface. For example, the flow-modifying device can be a bioabsorbable surface that substantially blocks fluid flow contacting an implanted device within a branched array of vein vessels, diverting fluid flow to other branches of the vein vessel array. In other embodiments, a flow-modifying device can maintain, regulate or vary the volume, speed or composition of the fluid contacting an interface. In one embodiment, the flow-modifying device can maintain, regulate or vary the rate of fluid flow across another flow-modifying device. Optionally, a flow-modifying device can also be positioned outside the lumen of a body vessel.

Illustrative Embodiments of a Fluid Control System

Figure 2A:
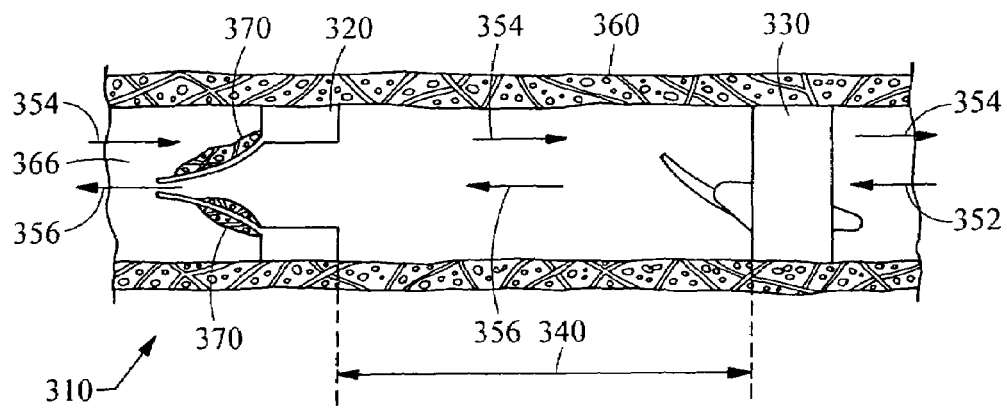
FIG. 2A, FIG. 2B and FIG. 2C are side cross-sectional views of selected fluid control system of embodiments of the invention.

FIG. 2A illustrates a fluid control system 310 of one embodiment of the invention. A tilting-disk valve 330 acts as a flow-modifying device positioned a flow-modifying effective distance 340 from a venous valve 320 interface comprising remodelable SIS leaflets within the lumen 366 of a body vessel 360 subject to a primary fluid flow 352 in a downstream direction. The venous valve 320 comprises two opposable leaflets that open to allow a modified fluid flow 356 to pass in one direction, but close to substantially prevent retrograde flow 354 in the opposite direction. Optionally, the venous valve 320 permits a controlled amount of retrograde flow 354 to pass toward the tilting disk valve 330. The tilting-disk valve 330 is a monoleaflet mechanical valve with both a disc and a housing ring constructed from pyrolytic carbon. A small amount of reflux flow 354 through the venous valve 320 interface can be permitted in a retrograde direction in one embodiment. As illustrated, the venous valve 320 interface comprises SIS leaflets, shown partially-remodeled by autologous tissue 370, which is shown along the leaflets of the valve and the portion of the venous valve engaging the body vessel 360. In one embodiment, the tilting-disk valve 330 flow-modifying device is biased to fail in the open or partially open position. Optionally, the tilting-disk valve 330 flow-modifying device is adapted to allow a small amount of retrograde fluid flow 354 in a retrograde direction when the body vessel 360 is a vein. The valve flow-modifying device 330 can modify the primary fluid flow 352 to a modified fluid flow 356 that contacts the venous valve 320 interface.

Figure 2B:
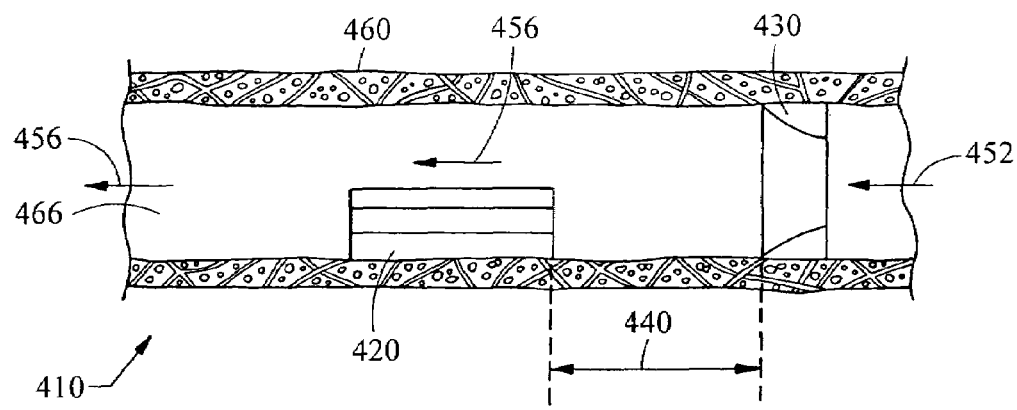

FIG. 2B illustrates a fluid control system 410 of another embodiment of the invention. A flow reducing flow-modifying device 430 is positioned a flow-modifying effective distance 440 from an interface 420 within the lumen 466 of a body vessel 460. The flow reducing flow-modifying device 430 reduces the rate of fluid flow without substantially altering the direction of fluid flow. Accordingly, a first fluid flow 452 enters the flow occluding flow-modifying device 430 in a downstream direction, and a reduced fluid flow 456 exits the flow-modifying device 430 in the downstream direction. The second fluid flow 456 contacts the interface 420. Optionally, the flow reducing flow-modifying device 430 can further comprise a bioabsorbable wall that substantially or completely blocks primary fluid flow 452, so that the modified fluid flow 456 is negligible.

Figure 2C:
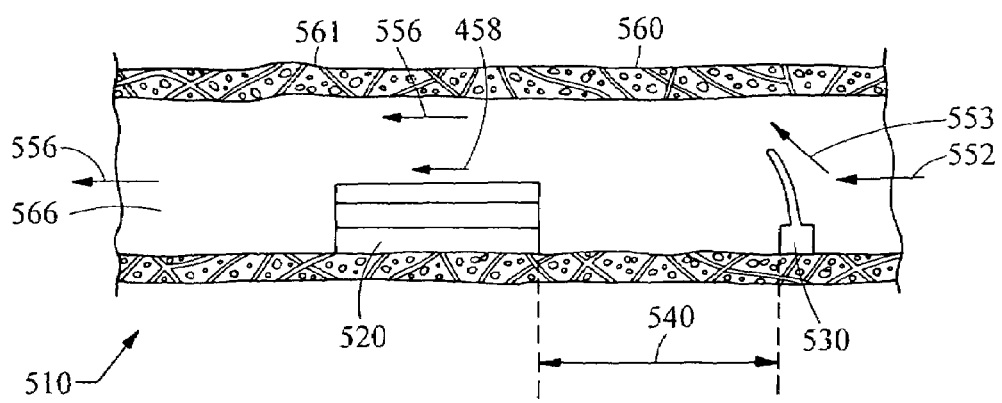

FIG. 2C illustrates a fluid control system 510 of another embodiment of the invention. A flow directing flow-modifying device 530 is positioned a flow-modifying effective distance 540 from an interface 520 within the lumen 566 of a body vessel 560. The flow directing flow-modifying device 530 alters the direction of fluid flow. A primary fluid flow 552 enters the flow directing flow-modifying device 530 in a downstream direction and is deflected in a first direction 553 off of the flow-modifying device 530. A modified fluid flow 556 is substantially confined along a wall 561 of the body vessel 560 distal to the interface 520, so that a reduced fluid flow 458 contacts the interface 520. The interface 520 contacts the second fluid flow 556 in a manner that preserves, promotes, alters or enhances a desired surface-mediated process on the surface of the interface 520.

As illustrated by a comparison of FIG. 2A, FIG. 2B, and FIG. 2C, the phrases "fluid flow across an interface," "fluid flow contacting an interface" and "fluid flow in contact with an interface" refer to the fluid that actually contacts the interface, whether or not the fluid also contacts the flow-modifying device. For example, in one embodiment, fluid flows directly across both the flow-modifying device and the interface. In one embodiment, fluid does not directly contact both the flow-modifying device and the interface. In FIG. 2A, the primary fluid flow 352 contacts the tilting-disk valve 330 flow-modifying device, which acts to regulate the modified fluid flow 356 actually contacting the venous valve 320 interface. In FIG. 2B, the flow-modifying device 430 reduces the primary flow 452 so that the interface 420 is subjected to a reduced fluid flow 456. In FIG. 2C, the flow directing flow-modifying device 530 redirects a primary fluid flow 552 so that the interface is subject to the reduced (negligible or substantially reduced) fluid flow 458. All three flow-modifying device embodiments of FIG. 2A, FIG. 2B, and FIG. 2C can modify the fluid flow actually contacting the interface in each instance.

Characteristics of Flow-Modifying Device Materials

A variety of devices are available for providing a flow-modifying device, as one skilled in the art will appreciate. A suitable flow-modifying device preferably provides the capability of altering or varying the fluid flow across an interface in a manner that preserves, promotes, alters, or enhances a desired process at the interface. In one embodiment, the flow-modifying device reduces or prevents fluid flow along one portion of a branched network of body vessels, such as veins. In one embodiment, the flow-modifying device is made of remodelable or bioadsorbable material. In one embodiment, the flow-modifying device is made of material that dissolves gradually so as to provide temporary flow modification while the interface is most sensitive to fluid flow.

In one embodiment, the flow-modifying device can withstand large and rapid pressure changes, mechanical stress created by continuous opening and closing, and resistance to gradual change in physical and/or structural properties that may produce deterioration. In some embodiments, the flow-modifying device is a mechanical valve. In one embodiment, the flow-modifying device comprises patient-compatible materials that are thromboresistant and have a very low density. Furthermore, in one embodiment, the flow-modifying device can be constructed to withstand long term usage and wear, without fatigue, breakage or fracture of the valve components.

The flow-modifying device can be formed from a variety of suitable materials known in the art. In one embodiment, the flow-modifying device can comprise material that is resorbed by the body after remodeling at an interface is completed. In one embodiment, the flow-modifying device can comprise other materials such as polyacetal resins known as DERLIN® (product name of DuPont Corp., USA), Carbon/pyrolite, or a suitable bioabsorbable material.

In certain preferred embodiment, the flow-modifying function of a flow-modifying device varies with time, for example as a portion of the flow-modifying device comprising a bioabsorbable material is absorbed. A number of bioabsorbable homopolymers, copolymers, or blends of bioabsorbable polymers are known in the medical arts that can be used in providing a flow-modifying device. These include, but are not necessarily limited to, poly-alpha hydroxy acids such as polyactic acid, polylactide, polyglycolic acid, or polyglycolide; trimethlyene carbonate; polycaprolactone; poly-beta hydroxy acids such as polyhydroxybutyrate or polyhydroxyvalerate; or other polymers such as polyphosphazines, polyorganophosphazines, polyanhydrides, polyesteramides, polyorthoesters, polyethylene oxide, polyester-ethers (e.g., polydioxanone) or polyamino acids (e.g., poly-L-glutamic acid or poly-L-lysine). There are also a number of naturally derived bioabsorbable polymers that may be suitable, including modified polysaccharides such as cellulose, chitin, and dextran or modified proteins such as fibrin and casein.

In one embodiment, the flow-modifying device is a bioprosthetic valve. Bioprosthetic valves can be made from porcine or bovine material that may be attached to a metal or plastic frame. In one embodiment, the flow-modifying device is a mechanical prosthetic valve. A variety of mechanical prosthetic valves are known in the art, which include the valves discussed below.

Open-Biasing of Mechanical Valve Flow-Modifying Devices

In one embodiment, the flow-modifying device is biased to fail in an open position so as to allow continued contact of fluid in the lumen with the interface after failure of the flow-modifying device. One such open-biased valve that can, in one embodiment, provide a flow-modifying device is a variation of the valve presented by U.S. Pat. No. 4,605,408, issued Aug. 12, 1986 to Alain Carpentier. According to the teaching of the '408 patent, the leaflets of a mechanical valve are biased toward an open position by either a leaf spring device effective while the leaflets are close to their seats, or by a pair of magnets repelling one another. One of the magnets of each pair of magnets is carried in a leaflet, while the other magnet of each pair is carried by the base member adjacent to the valve seat. The magnets are oriented to repel one another. As a consequence, the valve leaflets are urged away from their seats. The effective bias provides a closing cushion as the leaflets approach their seats, and also urges the leaflets off their seat to provide an anticipatory opening of the valve.

Any number of mechanical valves known in the art, including those discussed below, can be modified where necessary to provide a failure mode that leaves the valve in the open, or partially open position.

Caged-Ball Mechanical Valves as Flow-Modifying Devices

In one embodiment, the flow-modifying device is a caged-ball valve. Caged-ball valves consist of generally three or four struts attached to a ring that is inserted in either the mitral or the aortic position. Contained within the valve struts is a silastic ball, which controls the flow of blood through the valve. A number of caged ball valves are known in the art, including those developed by Starr-Edwards, Harken devices including the Serville-Arbonville, Harken-Daval, Cooley-Cromie, Debakey-Surgitool, and Smeloff-Cutter models. Relevant presentations of various caged ball valves known in the art include: Fann, James I., Carlos E. Moreno-Cabral, and D. Craig Miller, "Caged-Ball Valves: The Starr-Edwards and Smeloff-Sufter Prostheses," *Replacement Cardiac Valves*. Ed. Endre Bodnar and Robert Frater. New York: Pergamon Press, 149-186 (1991), and Lefrak, Edward A. and Albert Starr, eds. *Cardiac Valve Prostheses*. New York: Appleton-Century-Crofts, 3-32.

Central Flow Mechanical Valves as Flow-Modifying Devices

In one embodiment of the invention, the flow-modifying device is a central flow valve, which are designed to imitate natural valves. See McGoon, D. C., "The Status of Prosthetic Cardiac Valves," Biological Tissue in Heart Valve Replacement. Ed. M. I. Ionescu, D. N. Ross, and G. H. Wooler, London: Butterworths, 3-17.

Disc Mechanical Valves as Flow-Modifying Devices

In one embodiment, the flow-modifying device of the invention is a tilting disc valve. Tilting disc valves have a lower profile than caged-ball valves. Instead of a ball, these valves utilize a disc which is tilted such that blood flow is less obstructed in an open position. One example is the Bjork-Shiley valve. This valve has a free-floating disc retained by a low-profile M-shaped strut on the inflow side and a U-shaped strut on the outflow side of the valve. The original version is capable of pivoting to an opening of 60 degrees, while later versions provided a convexo-concave shape and were available with an opening of either 60 or 70 degrees. Two other examples are the Omniscience and the Medtronic Hall valves, which are commonly used tilting disc valves in the United States. Relevant information on tilting disc valves can be found in Bain, William H., and S. A. M. Nashef, "Tilting Disc Valves," Replacement Cardiac Valves. Ed. Endre Bodnar and Robert Frater, New York, Pergamon Press, 187-200 (1991).

Bileaflet Mechanical Valves as Flow-Modifying Devices

In one embodiment, the flow-modifying device is a bileaflet mechanical valve. Mechanical valves of the bileaflet type typically comprise a pair of flat leaflets pivotally mounted within a ring-like annular valve body. The leaflets will pivotally move, in response to hemodynamic movement of a body fluid, for example blood, between an "open" position whereby the body fluid is permitted to flow through the annular valve body in a first direction, and a "closed" position whereby blood is prevented from backflowing in a second direction opposite said first direction.

In one embodiment, the flow-modifying device is a prosthetic valve of the bileaflet type constructed in a manner which will minimize or prevent the lodging or stagnation of blood within specific regions of the valve, as such stagnation or lodging of blood may result in thrombus formation and the occurrence of associated thromboembolic complications. In particular, one area where blood cells may tend to lodge or stagnate within the hinge or pivot mechanism is the occluder leaflets attached to the annular valve body. Accordingly, some valves can incorporate modified pivot/hinge mechanisms capable of carrying out a self-clearing or self-"washing" function to remove any lodged or stagnating blood cells from the hinge or pivot mechanism. Alternatively, valves can be configured to allow a controlled amount of retrograde flow, for example to prevent stagnation of fluid.

In one embodiment, the flow-modifying device is a bileaflet mechanical prosthetic valve designed such that the leaflets will open and close softly, without slamming or unnecessary surface-to-surface contact, so as to minimize the likelihood of hemolysis (i.e., the breaking or rupture of blood cells). Two commonly implanted bileaflet valves are the Sultz-Carbomedics valve.

In one embodiment, the flow-modifying device is a bileaflet mechanical valve according to U.S. Pat. No. 4,276,658, issued Jul. 7, 1981, assigned to St. Jude Medical, Inc., of St. Paul, Minn., and disclosing what is generally known as the "St. Jude Valve." This mechanical valve includes a base portion defining a through blood passageway and pivotally carrying a pair of valve leaflets. The valve leaflets are sealingly cooperable with each other and with the base member to occlude the blood passageway. Alternatively, in response to dynamic blood fluid forces, the leaflets are pivotal to another position opening blood flow in one direction through the blood passageway. The dynamic blood fluid forces are able to pivot the leaflets between their open and closed positions to allow peristaltic pumping of fluid through a body vessel in which the valve is installed.

Another type of bileaflet mechanical valve, designed by Gott-Daggett, replaces the ball or disc of the prior valves with two semicircular leaflets retained within the ring by two struts.

For information concerning bileaflet valves, one helpful reference is Horstkotte, Dieter and Endre Bodnar, "Bileaflet Valves," *Replacement Cardiac Valves*, Ed. Endre Bodnar and Robert Frater, New York, Pergamon Press, 201-228 (1991).

Other Valves as Flow-Modifying Devices

Still another example of a flow-modifying device useful in certain embodiments of the present invention is the implantable valve described in U.S. Pat. No. 6,602,296 to Strecker. Other examples of flow-modifying devices include valves described in the following U.S. Pat. No. 4,178,639 (Bokros), U.S. Pat. No. 4,272,854 (Bokros), U.S. Pat. No. 4,276,658 (Hanson, et al.), U.S. Pat. No. 4,328,592 (Klawitter), U.S. Pat. No. 4,363,142 (Meyer), U.S. Pat. No. 4,373,216 (Klawitter), U.S. Pat. No. 4,443,894 (Klawitter), U.S. Pat. No. 4,451,937 (Klawitter), U.S. Pat. No. 4,605,408 (Carpentier), U.S. Pat. No. 4,446,577 (Meyer, et al.), U.S. Pat. No. 4,676,789 (Sorensen, et al.), U.S. Pat. No. 4,692,165 (Bokros), U.S. Pat. No. 4,822,353 (Bokros), U.S. Pat. No. 4,863,458 (Bokros), U.S. Pat. No. 4,863,459 (Olin), U.S. Pat. No. 4,872,875 (Hwang), U.S. Pat. No. 4,888,010 (Bokros), U.S. Pat. No. 4,892,540 (Vallana), U.S. Pat. No. 4,923,465 (Knoch, et al.), U.S. Pat. No. 4,935,030 (Alonso), U.S. Pat. No. 4,995,881 (Knoch, et al.), U.S. Pat. No. 5,002,567 (Bona, et al.), U.S. Pat. No. 5,061,278 (Bicer), U.S. Pat. No. 5,078,738 (Couetil), U.S. Pat. No. 5,108,425 (Hwang), U.S. Pat. No. 5,116,366 (Hwang), U.S. Pat. No. 5,116,367 (Hwang, et al.), U.S. Pat. No. 5,123,920 (Bokros), U.S. Pat. No. 5,137,532 (Bokros, et al), U.S. Pat. No. 5,147,390 (Campbell), U.S. Pat. No. 5,152,785 (Bokros, et al.), U.S. Pat. No. 5,171,263 (Boyer, et al.), U.S. Pat. No. 5,178,632 (Hanson), U.S. Pat. No. 5,192,309 (Stupka, et al.), U.S. Pat. No. 5,192,313 (Budd, et al.), U.S. Pat. No. 5,197,980 (Gorshkov, et al.), as well as the following foreign patents and foreign patent publications: EP238181A, WO 86/05383, WO 91/11973, 0091746, 0465383A1, 0541215A1, WO 92/21305, 0023797, GB2055,452A, 0050439, GB2018396A, 0515324A1, WO92/02197, 0327790, EP289494, EP133608A, WO93/01767, EP89104A, EP256047A, EP436420A, EP 403649A, WO90/04367, EP176237A, and WO91/05524.

For a review of various mechanical valves that can provide a flow-modifying device in some embodiments of the invention, see deWall et al., "Evolution of Mechanical Heart Valves," *Ann. Thorac. Surg.*, 69, 1612-1621 (2000), which is incorporated herein by reference. Examples discussed therein of possible flow-modifying devices, which are useful in some embodiments of the invention, include: the Harken-Soroff ball valve, the Starr-Edwards ball valve, the Magovern-Cromie ball valve, the Smelloff-SCDK-Cutter ball valve, the DeBakey-Surgitool caged ball valve, the Braunwald-Cutter ball valve, Bamard-Goosen nontilting disc valve, the Kay-Suzuki caged disc valve, the Cross-Jones caged lens prosthesis, the Kay-Shiley disc valve with muscle guard, the Lillehei-Nakib toroidal valve, the Beall-Surgitool disc valve, the Davila-Sierra sliding disc valve, the Cooley-Cutter bionical disc prosthesis, the Lellehei-Curz-Kaster tilting disc valve, the Wada-Cutter tilting disc valve, the Lellehei-Kaster tilting disc prosthesis, the Omniscience and Omnicarbon valves, the Bjork-Shiley tilting disc valve, the Medtronic-Hall-Kaster tilting disc, the Gott-Daggett valve, the Lillehei-Kalke bileaflet prosthesis, and the St Jude bileaflet prosthesis.

Body Vessel Occluding Devices as Flow-Modifying Devices

In some embodiments, a flow-modifying device substantially prevents the flow of fluid at an interface. In some embodiments, the flow-modifying device permanently occludes a body vessel. In other embodiments, the flow-modifying device temporarily temporarily occludes a body vessel. Any suitable occluding device can be used as a flow-modifying device to block fluid flow in a body vessel. For example, U.S. Pat. No. 5,334,210, entitled "Vascular occlusion assembly" and U.S. Pat. No. 5,222,970, entitled "Method of and system for mounting a vascular occlusion balloon on a delivery catheter," are both incorporated herein by reference in their entirety as examples of a flow-modifying devices. Optionally, the flow-modifying device comprises a bioabsorbable material and the flow-modifying device is implanted within a body vessel such as a vein, to permit fluid flow to contact an interface after absorption of a portion of the bioabsorbable material.

Embodiments comprising a flow-modifying device of the present invention are not restricted to the placement of the flow-modifying device in or near the heart or in an artery of a body. Rather, the flow-modifying device can be placed in any position or configuration that provides for maintaining, regulating or varying the fluid flow across an interface in a manner that preserves, promotes, alters, or enhances a desired process at the interface.

Flow-Modifying Effective Distances

In some embodiments, the interface is separated from a flow-modifying device by a distance effective to modify fluid flow at the interface, within the lumen of a body cavity. A "distance effective to modify fluid flow," and "flow-modifying effective distance," as used herein, mean any relative positioning of the interface and the flow-modifying device with respect to each other, at a static or dynamic distance or orientation, whereby the flow-modifying device is able to maintain, regulate or vary the fluid contacting the interface so as to preserve, promote, alter, or enhance a desired process at the interface. "Positioning" of the interface or flow-modifying device includes both the relative distance between the interface and the flow-modifying device, as well as the orientation (including tilting, rotation, and the like) of the interface and the flow-modifying device relative to each other. Preferably, the flow-modifying device and the interface are positioned at a flow-modifying effective distance relative to each other within a continuous body vessel such as a vein.

The distance between the flow-modifying device and the interface are measured along a body vessel, for example, by remote displacement of the distal end of a catheter within a body vessel. The distance can also be measured by other techniques, such as by using imaging techniques like ultrasound, x-rays, or magnetic resonance imaging, and the like, of a body cavity. In other embodiments, a device comprising the interface or the flow-modifying device can comprise a marker designed to be visible by one or more remote imaging techniques, such as x-rays, magnetic resonance imaging, or ultrasound.

In one embodiment, multiple flow-modifying devices can each be positioned at various flow-modifying effective distances from one or more flow-modifying devices. In one embodiment, the flow-modifying device and the interface are positioned at a flow-modifying effective distance along a branched body vessel, and the flow-modifying effective distance is measured by the distance of the path along the body vessel between the flow-modifying device and the interface.

In some embodiments, the flow-modifying effective distance can be measured along the alimentary canal, for example with respect to the esophageal or pyloric sphincter, or within a biliary duct. For example, the flow-modifying device can reduce or prevent acid reflux in the esophagus. In another embodiment, the flow-modifying effective distance can be measured along the ureter or urethra, or within a kidney. In another embodiment, the flow-modifying distance can be measured along an artery or with respect to a heart valve.

In certain embodiments, a flow-modifying effective distance can be selected based in whole or in part on human or animal venous anatomy. Veins are blood vessels that return blood to the heart. Veins are able to increase in diameter when filled. The saphenous veins and their branches are superficial veins above the muscles of the leg. Larger deep veins lie within the muscle compartments and carry most of the blood out of the leg. In some embodiments, a flow modifying venous valve is transluminally implanted within a deep vein. Deep veins generally follow the path of associated arteries. The tibial or peroneal vein is located in the calf, the popliteal vein is located behind the knee, and the femoral vein is located in the thigh. The superficial and deep veins are connected by perforator veins. Many veins have venous valves that are one-way valves composed of two leaflets that close together when filled with blood. When closed, venous valves prevent blood from flowing back (refluxing) into the leg. If these valves become damaged and fail to function properly (become incompetent) blood can become static in the leg. Pressurization of venous valves is a result of gravity during constant upright pressure and may lead to enlargement of the veins (varicose veins), pain, leg swelling, skin discoloration (hyperpigmentation), and even skin breakdown (ulcers).

In some embodiments, the flow-modifying distance can correspond to the congenital distance between venous valves along a segment of vein. In one embodiment, the flow-modifying effective distance is measured along the lumen of a body vessel. In one embodiment, the flow-modifying effective distance is measured along a conduit connected to a flow-modifying device, where the conduit is inserted into the body vessel. In some em-*+bodiments, the flow-modifying effective distance can be less than about 100, 90, 80, 70, 60, 50, 40, 30, 20, or 10 cm, less than 10, 9, 8, 7, 6, 5, 4, 3, 2, or 1 cm, or less than 1 cm, depending on the location of the interface and the flow-modifying device.

In one embodiment, the flow-modifying effective distance is measured at least in part along the cephalic, basilica or great saphenous veins that originate from the acral venous network and flow into the proximal deep veins and to venous roots in communication with these veins. Placement of flow-modifying devices or an interface can be informed, for example, by a recent study of the location of venous valves within the cephalic, basilica and great saphenous veins discloses the distribution of cutaneous venous valves, and is incorporated herein by reference. Akira Iimura, et al., "Anatomical Study of distribution of valves of the cutaneous veins of adult's [sic.] limbs," *Ann. Anat* 185:91-95 (2003).

In some embodiments, the flow-modifying effective distance is measured along the cephalic, basilica or great saphenous veins.

In one embodiment, the flow-modifying effective distance can be measured along at least part of a saphenous vein, and can be less than about 75, 65, 55, 45, 35, 25, 15, 10 or 5 cm, preferably less than 50, 40, 30, 20, 10, or 1 cm, and more preferably less than about 15, 14, 13, 12, 11, 10, 9, 8, 7, 6, 5, 4, 3, 2 or 1 cm.

In one embodiment, the flow-modifying effective distance can be measured in part along the superficial femoral popliteal vein, and can be less than about 30 cm. For example, the flow-modifying distance can correspond to a distance of about 1 mm-15 cm, as observed, for example, between naturally occurring but defective venous valves. The length and disposition of venous valves along the superficial femoral popliteal vein is discussed, for example, by S M Santilli et al., "Superficial femoral popliteal vein: An anatomical study," *J Vasc Surg*, 31(3): 450-455 (2000), which is incorporated by reference.

In one embodiment, the flow-modifying effective distance can be less than about 5.0 cm, preferably less than about 2.0 cm, above the union of the subclavian vein and the internal jugular vein. In one embodiment, the flow-modifying effective distance corresponds to the distance between a natural venous valve and the subclavian and internal jugular vein junction, which on average is about 1.7 cm. Harmon, J V et al., "Venous valves in subclavian and internal jugular veins; Frequency, position and structure in 100 autopsy cases," *Am J Cardiovasc Pathol*, 1(1):51-54 (Jan. 1987). The flow-modifying distance can be determined based on the anatomy and competency of venous valves in this area, as discussed, for example, by M. Imai et al., "Valve injury: a new complication of internal jugular vein cannulation," *Anesth Analg.*, 78(6): 1039-40 (1994).

In some embodiments, the flow-modifying effective distance is between about 1 mm and 50 mm. For example, in one embodiment, the flow-modifying distance is measured to be about 5 mm distal to the orifice of a venous valve root. The term "valve root" refers to a branching vessel bringing fluid flow toward a flow-modifying device, such as a valve as disclosed in Iimura et al. As another example, when a flow-modifying effective distance is measured along a vein in the upper limb, the distance can be about 2 mm-4 mm distal to a valve orifice. As another example, a flow-modifying distance can be between less than 30 cm, preferably less than 15 cm, or more preferably about 75 mm or less distal to a venous valve root in the great saphenous vein. In another embodiment, the flow-modifying distance can be situated in areas prone to vulnerability and disease that can be treated with a flow-modifying device and an interface. For example, Lajos et al., found that these distances corresponded to areas of vulnerability and disease along the long saphenous venous system that are less than 30 cm from the ankle, preferably 12 cm-16 cm or 20 cm-25 cm from the ankle along the long saphenous vein. In other embodiments, a flow-modifying distance can be between less than 35 mm, preferably less than 15 mm, or more preferably about 5 mm or less distal to a venous valve root in the cephalic vein. In other embodiments, a flow-modifying distance can be between less than 15 mm, preferably less than 10 mm, or more preferably about 5 mm or less distal to a venous valve root in the basilic vein.

In some embodiments, part of the flow-modifying effective distance can be measured in part along a vein with a diameter smaller than 2 mm, and preferably along a vein with a diameter of less than 300 µm, and the interface can be venous valves along such veins. Such micro-venous valves are discussed, for example, in Phillips, Minn., et al., "Micro-venous valves in the superficial veins of the human lower limb," *Clin. Anat.*, 17(1): 55-60 (2004), which is incorporated herein by reference.

Remodeling of Autologous Tissue

In one embodiment, the interface is SIS and the flow-modifying device is positioned at a flow-modifying effective distance from the interface so as to promote, preserve or enhance the remodeling of the implanted SIS material.

Investigations of remodeling of SIS within body vessels have shown that the remodeling process appears to begin within about 2 days after implantation of SIS and may continue for up to about 90 days, or longer. Without being limited to theory, a number of investigations (discussed below) show that SIS remodeling has been observed on a time scale of about a week to three months in different studies. Accordingly, in one embodiment, the flow-modifying device is provided for the time during which the remodeling of SIS is sensitive to the flow of contacting fluid. In one embodiment, the flow-modifying device is provided for about 6 months, or longer. In one embodiment, the flow-modifying device is provided for about 90 days, or longer. In one embodiment, a flow-modifying device is provided for about 6 weeks. In one embodiment, a flow-modifying device is provided for about 4 weeks. In one embodiment, a flow-modifying device is provided for about 3 weeks.

In one investigation, researchers implanted a small caliber vascular graft from porcine small intestine submucosa in a canine carotid artery and compared the remodeling process with an autogenous saphenous vein graft implanted in the contralateral carotid artery. At 2 days after implant, the luminal surface of the SIS graft was covered with a thin (30 mu) fibrin meshwork. Smooth muscle cells were observed in the new intima (fibrin meshwork) by 28 days. By 90 days, both types of graft had arterialized with an intima covered by endothelium, a smooth muscle media and marked adventitial fibrosis. Similar histology was observed at 180 days. Sandusky et al., "Histologic findings after in vivo placement of small intestine submucosal vascular grafts and saphenous vein grafts in carotid artery in dogs," *Am. J. Pathol.*, 140(2), 317-24 (February 1992).

In another investigation, SIS venous conduit was implanted between the portal vein and inferior vena cava in Lewis rats. Smooth luminal surface with endothelial-like cells were observed on the implanted SIS material by 3 weeks. Subsequent histology of excised SIS venous grafts demonstrated a confluent luminal endothelial monolayer, absence of thrombus, and neovascularization in the SIS graft. Kim et al., "Small intestinal submucosa as a small-caliber venous graft: a novel model for hepatocyte transplantation on synthetic biodegradable polymer scaffolds with direct access to the portal venous system," *J. Pediatr. Surg.*, 34(1), 124-128 (January 1999).

Another study found that SIS vascular grafts explanted after about 60-days were found to be encased in fibrous tissue. Measurements of mechanical properties (compliance, elastic modulus and burst pressure) of the explanted remodeled grafts approached the mechanical properties of the original vessel, indicating that remodeled tissue on the SIS graft possessed similar mechanical properties. Roeder et al., "Mechanical remodeling of small-intestine submucosa small-diameter vascular grafts—a preliminary report," *Biomed. Instrum. Technol.*, 35(2), 110-120 (March 2001).

A study of SIS implanted in the abdominal wall of dogs and rats over a 2 year period indicated that SIS material appeared fully remodeled by 3 months. After 3 months, the SIS was no longer recognizable and appeared to be replaced by host tissue, including collagenous connective tissue, adipose tissue and bundles of skeletal muscle. Notably, SIS was observed to serve as a scaffold for new skeletal muscle tissue in this study. Badylak et al., "Morphologic Study of Small Intestinal Submucosa as a Body Wall Repair Device," *J. Surg. Research*, 103, 190-202 (April 2002).

A recent study of square stent-based bicuspid venous valves comprising small intestinal submucosa implanted in the venae cavae of adult sheep for 5 weeks showed remodeling of the SIS material. Remodeling was indicated by the presence of newly formed collagen fibers on the SIS, fibroblasts and inflammatory cells penetrating the SIS leaflets, endothelial cells on the surface of the SIS, and neovascularization of the SIS material. Endothelial cells were found on both surfaces of the SIS valve leaflets. Researchers concluded that the SIS-based valve remodeling occurred independently of vessel wall contact by recruitment of cells directly from circulation. Brountzos, et al, "Remodeling of suspended small intestinal submucosa venous valve: an experimental study in sheep to assess the host cells' origin," *J. Vasc. Interv. Radiol.*, 14(3), 349-356 (March 2003).

Accordingly, in one embodiment of the invention, the flow-modifying device can be adapted to maintain, regulate or vary the fluid contacting one or more interfaces implanted in a body vessel during a time period when the remodeling process can most effectively be preserved, promoted or enhanced. In one embodiment, the flow-modifying device can be removed after the remodeling process has sufficiently occurred. In one embodiment, the flow-modifying device can comprise resorbable material. In one embodiment, the flow-modifying device can be permanently implanted within the body.

Other investigations suggest that hemodynamic forces within a blood vessel environment can play a role in the regulation of cells that compose the blood vessel wall. Therefore, modifying or regulating the flow of fluid contacting an interface positioned within a blood vessel could favorably preserve, promote, alter, or enhance the remodeling process by allowing or promoting chemical changes in the body vessel lining that are favorable to remodeling. For example, shear stress on the endothelial cells lining blood vessels can induce activity of several shear stress-inducible genes including PDGF-A, PDGF-B, basic fibroblast growth factor (FGF) and nitric oxide synthase, all of which are implicated in wound remodeling. U.S. Pat. No. 6,572,650 to Abraham et al., incorporated herein by reference, discloses a study of in vivo remodeling of submocusal collagen material implanted in blood vessels wherein the remodeling process did not compromise the mechanical integrity of the implant, and the implant was susceptible to the same stress induced chemical changes undergone by endothelial blood vessels.

Accordingly, in one embodiment of the invention, the flow-modifying device can also be favorably positioned to preserve or alter the chemical environment in the fluid flow across the interface so as to preserve, promote, alter or enhance remodeling at the interface.

Multiple Interfaces and Multiple Flow-Modifying Devices

In one embodiment, where multiple flow-modifying devices or multiple interfaces are employed in fluid communication with each other, the interfaces and the flow-modifying devices are all in cooperative fluid flow communication.

"Cooperative fluid flow communication" means that the interfaces and flow-modifying devices do not substantially hinder or prevent the preservation, promotion, or enhancement of a desired process at an implanted interface.

In one embodiment, the flow-modifying device and the interface can be positioned in series or in parallel at a flow-modifying effective distance within a continuous or a branched body vessel. In one embodiment, two or more interfaces are implanted in a body vessel and each interface is implanted at a flow-modifying effective distance from at least one flow-modifying device. In one embodiment, the interface is in fluid communication with a flow-modifying device. Where multiple interfaces are present in a body vessel, the fluid flow contacting each interface can be in the same or different directions. A flow-modifying device can affect fluid flow at one or more interfaces, in any suitable manner.

Figures 3A, 3B, 3C:
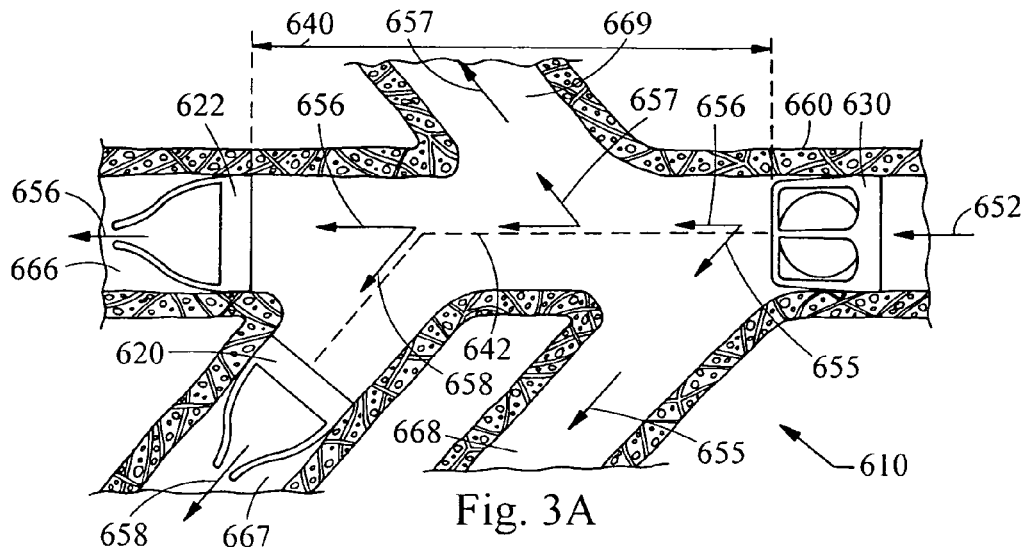
FIG. 3A, FIG. 3B and FIG. 3C are a side cross-sectional views of implantable intraluminal fluid flow control systems in a branched vessel.

FIG. 3A illustrates one embodiment of the invention comprising multiple venous valve interface devices in a parallel configuration within a branched body vessel network. A fluid flow control portion of a body vessel 610 comprises a branched body vessel 660. The branched body vessel 660 comprises a central lumen 656, a first branch lumen 655, a second branch lumen 657, and a third branch lumen 658. The fluid flow control system 610 comprises a caged ball flow-modifying device 630, a first venous valve interface 620 and a second venous valve interface 622, all disposed within the lumen 666 of a branched body cavity 660. The first venous valve interface 620 and the second venous valve interface 622 are intraluminally implanted venous valves comprising remodelable SIS leaflets. A first fluid flow 652 entering the flow-modifying device 630 in a first downstream direction divides into a second fluid flow 655 along a second downstream direction, a third fluid flow 657 along a third downstream direction, a fourth fluid flow 658 along a third downstream direction, and a fifth fluid flow 656 along the first downstream direction. The first interface 620 is positioned at a first flow-modifying effective distance 640 from the flow-modifying device 630. The second interface 622 is positioned at a second flow-modifying effective distance 642 (the dashed line) from the flow-modifying device 630. The first venous valve interface 620 and the second venous valve interface 622 are also positioned to be in cooperative fluid flow communication. Although not shown in FIG. 3A, in one embodiment, one or more of the fluid flows (655, 656, 657, and 658) can optionally be permitted to move in an opposite, retrograde, direction.

FIG. 3B shows a fluid flow control portion 680 of a branched vein network 681. A bioabsorbable flow reducing ring 690 flow modifying device is positioned a flow modifying effective distance from an intraluminally implanted venous valve 695a within a branched vein network 681. The branched vein network 681 comprises a central lumen 682, a first branch lumen 696, a second branch lumen 698, and a third branch lumen 694. The primary fluid flow 684a separates into a first diverted fluid flow portion 686a along both the first branch lumen 696 and the second branch lumen 698, and a central fluid flow 687a that contacts the flow reducing ring 690. The portion of the central fluid flow 687a that passes through the flow reducing ring 690 forms a modified fluid flow 688a. A portion of the modified fluid flow 688a forms a second diverted fluid flow 688a along the third branch lumen 694. The remaining portion of the modified flow 688a contacts an implanted venous valve 695a interface that comprises two leaflets 699a. The leaflets 699a comprise a remodelable material. The presence of the bioabsorbable flow reducing ring 690 reduces the fluid contacting the leaflets 699a of the venous valve until the flow reducing ring 690 is absorbed.

FIG. 3C shows a fluid flow control portion 670 of a branched vein network 671. A cuff 695b around a portion of the vein is a flow modifying device positioned a flow modifying effective distance from a natural incompetent venous valve 699b within a branched vein network 671. The cuff 695b constricts the vein to prevent fluid from flowing through the incompetent venous valve 699b, and diverting fluid flow 688b along a third branch lumen 674. The cuff 695b can be temporary bioabsorbable implant, or a more permanent non-bioabsorbable implant. The cuff 695b can be formed from any suitable material, including synthetic fabrics, injectable bulking agent gels, remodelable material, or tissue. The branched vein network 671 comprises a central lumen, a first branch lumen, a second branch lumen 675, and a third branch lumen 674. The primary fluid flow 684b separates into a first diverted fluid flow portion 686b along both the first branch lumen and the second branch lumen 675, and a central fluid flow 687b that forms a redirected portion 688b upon contact with the portion of the vein constricted by the cuff 695b. Optionally, a first prosthetic venous valve 673 can be intraluminally placed within the third branch lumen 674. Also optionally, a second prosthetic venous valve 672 can be intraluminally placed within the second branch lumen 675.

Figure 4:
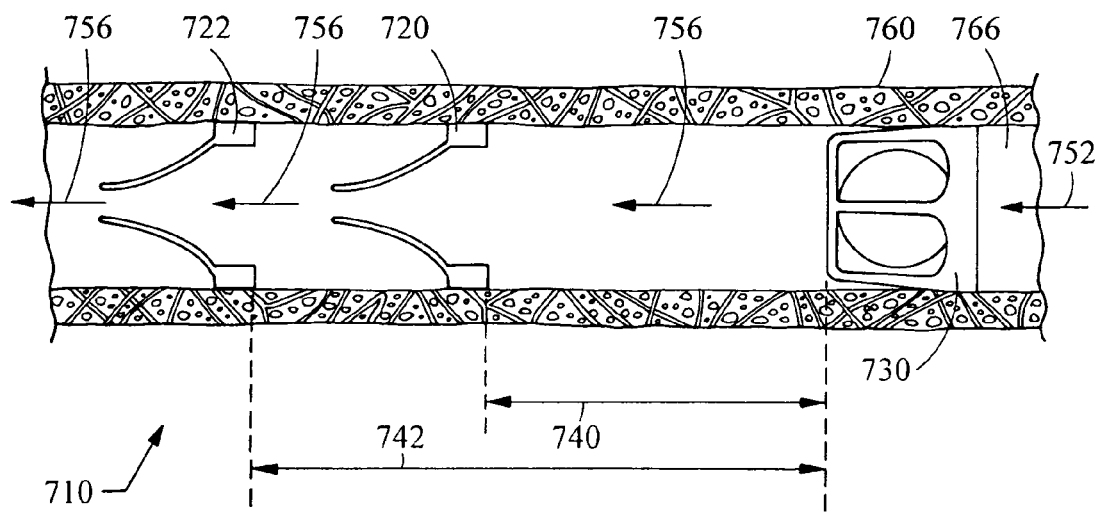
FIG. 4 is a side cross-sectional of an implantable intraluminal fluid flow control system comprising multiple venous valve interfaces positioned in series with an upstream caged ball valve flow-modifying device, according to one embodiment of the invention.

FIG. 4 illustrates one embodiment of the invention comprising multiple venous valve interface devices in a serial configuration. The fluid flow control system 710 comprises a caged ball flow-modifying device 730, a first venous valve interface 720 and a second venous valve interface 722, all disposed within the lumen 766 of a continuous body vessel cavity 760. A primary fluid flow 752 entering the flow-modifying device 730 in a downstream direction, leaves the flow-modifying device 730 as a modified fluid flow 756 that flows through the first interface 720 and the second interface 722. The first interface 720 is positioned at a first flow-modifying effective distance 740 from the flow-modifying device 730. The second interface 722 is positioned at a second flow-modifying effective distance 742 from the flow-modifying device 730. The first interface 720 and the second interface 722 are also positioned to be in cooperative fluid flow communication (not depicted in the figure). Although not shown in FIG. 4, in one embodiment, the fluid flows can be permitted to move in an opposite, retrograde, direction (not shown).

Combining a Flow-Modifying Device and an Interface in a Single Medical Device

Figure 5:
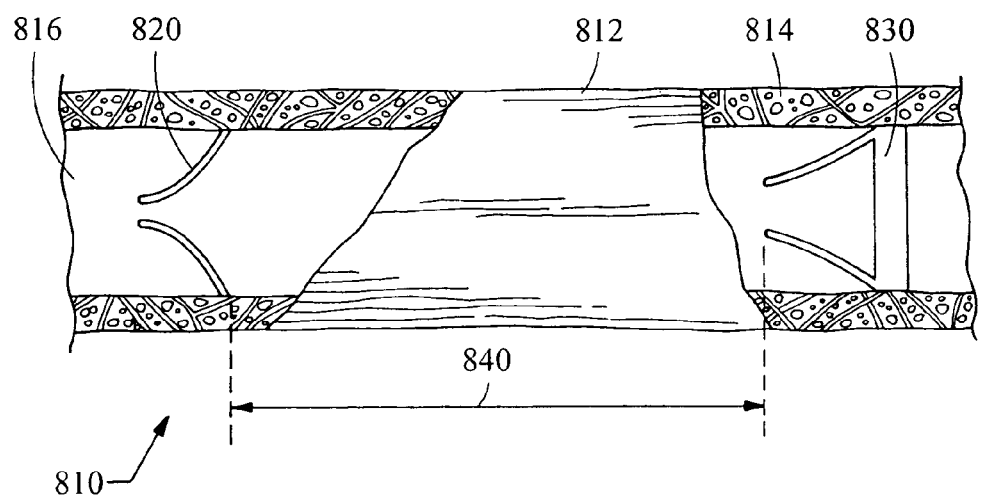
FIG. 5 is a side cross-sectional, partially broken away, of a medical device comprising an interface and a flow-modifying device, according to one embodiment of the invention.

In one embodiment, the flow-modifying device and the interface can be operatively connected in a single implantable medical device. FIG. 5 shows a cutaway view of an implantable medical device 810 comprising a venous valve interface 820 and a bileaflet valve flow-modifying device 830 positioned within a housing member 812. The housing member 812 comprises a tubular wall 814 defining an interior passage 816, wherein the interface 820 and the flow-modifying device are fixedly positioned at a flow-modifying effective distance 840. In one embodiment, the tubular wall 814 can comprise an expandable balloon that expands to secure the implantable medical device 810 in the lumen of a body vessel. In one embodiment, the tubular wall comprises a vessel engaging member (such as a suture, a barb, and the like) to securably position the implantable medical device 810 in the lumen of a body vessel. The housing member 812 can be made from any suitable biocompatible material, including stainless steel, a superelastic alloy such as NiTi (e.g., NITINOL™), a cobalt-chromium alloy, and the like. Preferably, the implantable medical device 810 is adapted for intraluminal delivery using a catheter delivery system. Accordingly, the implantable medical device 810 can have a compressed delivery configuration that can be placed inside the distal end of a catheter for delivery within a body vessel such as a vein. Preferably, the compressed configuration has a diameter of about 5-15 French. Preferably, the implantable medical device 810 is moveable between the compressed delivery configuration and a radially expanded deployment configuration within a vein. An implantable medical device 810 is preferably delivered with a catheter delivery system, such as those described herein. Preferably, the implantable medical device 810 is expanded from the compressed delivery configuration to the expanded deployment configuration within a vein, for example by expanding a balloon or by self-expansion of the implantable medical device 810 comprising a self-expanding material such as a NiTi alloy.

Delivery

The flow-modifying device and the interface can be delivered to the lumen of a body vessel by various techniques known in the art. In one embodiment, the flow-modifying device or the interface can be implanted in a body vessel through the use of a catheter. In one embodiment, the interface is adapted to be collapsible to fit within the lumen of the catheter, the catheter is then introduced into the body vessel and its tip positioned at a first point of treatment within the body vessel, and the interface is expelled from the catheter. In one embodiment, the interface is part of a resiliently biased and expandable support structure that expands upon expulsion from the catheter so as to fixedly engage the interior wall of the body cavity, allowing removal of the catheter while leaving the interface deployed at the first point of treatment. In one embodiment, the interface is an expandable venous valve.

Various methods of delivery and implantation configurations of flow-modifying devices and interfaces are provided. The flow-modifying device, the interface, or both can be surgically implanted simultaneously or separately within the body by medically appropriate methods. Multiple devices comprising one or more interfaces, flow-modifying devices, or both can be deployed in a body vessel at multiple points of treatment. The interface or the flow-modifying device can be securably positioned in the lumen of a body vessel using a catheter, for example by inflating a balloon to engage the wall of the body vessel. Alternatively, the flow-modifying device or the interface can be surgically introduced to the lumen of a body vessel and secured by various medical methods known in the art.

In one embodiment, a medical device comprising an interface and a flow-modifying device can be introduced to a body vessel and fixedly secured therein by resilient expansion of the medical device from a catheter inserted in the body vessel, such as by inflation of a balloon member to secure the device, or by other means known in the art including sutures or barbs. Preferably, the flow-modifying device or the interface can be implanted intraluminally within the lumen of a body vessel. In one embodiment, the interface can be intraluminally implanted using a catheter delivery system, without resort to surgical procedures.

Various delivery systems and methods currently available are adaptable for delivering an interface or a flow-modifying device to positions within the lumen of a body vessel. For example, in one embodiment, the delivery catheter described in U.S. Pat. No. 6,607,555 to Patterson et al. can be adapted to such a use. In another embodiment, the catheter delivery systems of U.S. Pat. No. 6,582,394 to Reiss et al. or U.S. Pat. No. 6,395,017 to Dwyer et al. can be adapted to provide delivery. Other non-limiting examples of delivery systems useful with some embodiments of the present invention include the balloon expandable catheter delivery systems described by U.S. Pat. No. 6,419,685 to DiCaprio et al., U.S. Pat. No. 4,950,227 to Savin et al., U.S. Pat. No. 5,409,495 to Osborne, U.S. Pat. No. 5,403,341 to Solar, U.S. Pat. No. 5,108,416 to Ryan et al., as well as European Pat. Application No. EP 055 3960A1 to Lau et al. In some embodiments, delivery can be accomplished using systems disclosed in European patent applications Ser. No. 94116805.6 filed Nov. 10, 1994 (Publication No. 0657147) and Ser. No. 95114543.2 filed Sep. 15, 1995 (Publication No. 0701800A1), which describe a recapturable prosthetic implant system that includes a delivery device in which a substantial portion of the implant may be ejected from the delivery device to enable determination of whether the implant is in its proper location and orientation, and of the correct size. Other non-limiting examples of delivery systems useful with certain embodiments of the present invention include those disclosed in U.S. Pat. No. 6,544,268 to Lazarus, U.S. Pat. No. 6,346,118 to Baker et al., U.S. Pat. No. 6,045,557 to White et al., U.S. Pat. No. 5,976,153 to Fischell et al., and U.S. Pat. No. 5,769,887 Brown et al. Other delivery systems suitable for implanting a flow-modifying device, an interface, or a medical device comprising both a flow-modifying device and an interface are provided by: U.S. Patent Published Patent Application Nos. US2004/0236346-A1 entitled "Delivery catheter and method of manufacture," and US2003/0144670-A1 entitled, "Medical device delivery system," as well as U.S. Pat. No. 5,250, 038 entitled, "Multiple lumen vascular access introducer sheath," and U.S. Pat. No. 5,643,317 entitled, "Closure prosthesis for transcatheter placement," all of which are incorporated herein by reference in their entirety.

Kits

In one embodiment, the invention provides a kit useful in controlling intraluminal flow at an interface in a body vessel. In one embodiment, the kit comprises an implantable interface and an implantable flow-modifying device. In another embodiment, the kit further comprises multiple interfaces, or multiple flow-modifying devices. In one embodiment, the kit comprises an implantable medical device comprising both a flow-modifying device and an interface in operative communication to each other. In one embodiment, the kit can further comprise a delivery means for introducing the interface, flow-modifying device, or a medical device into the lumen of a body vessel.

Figure 6:
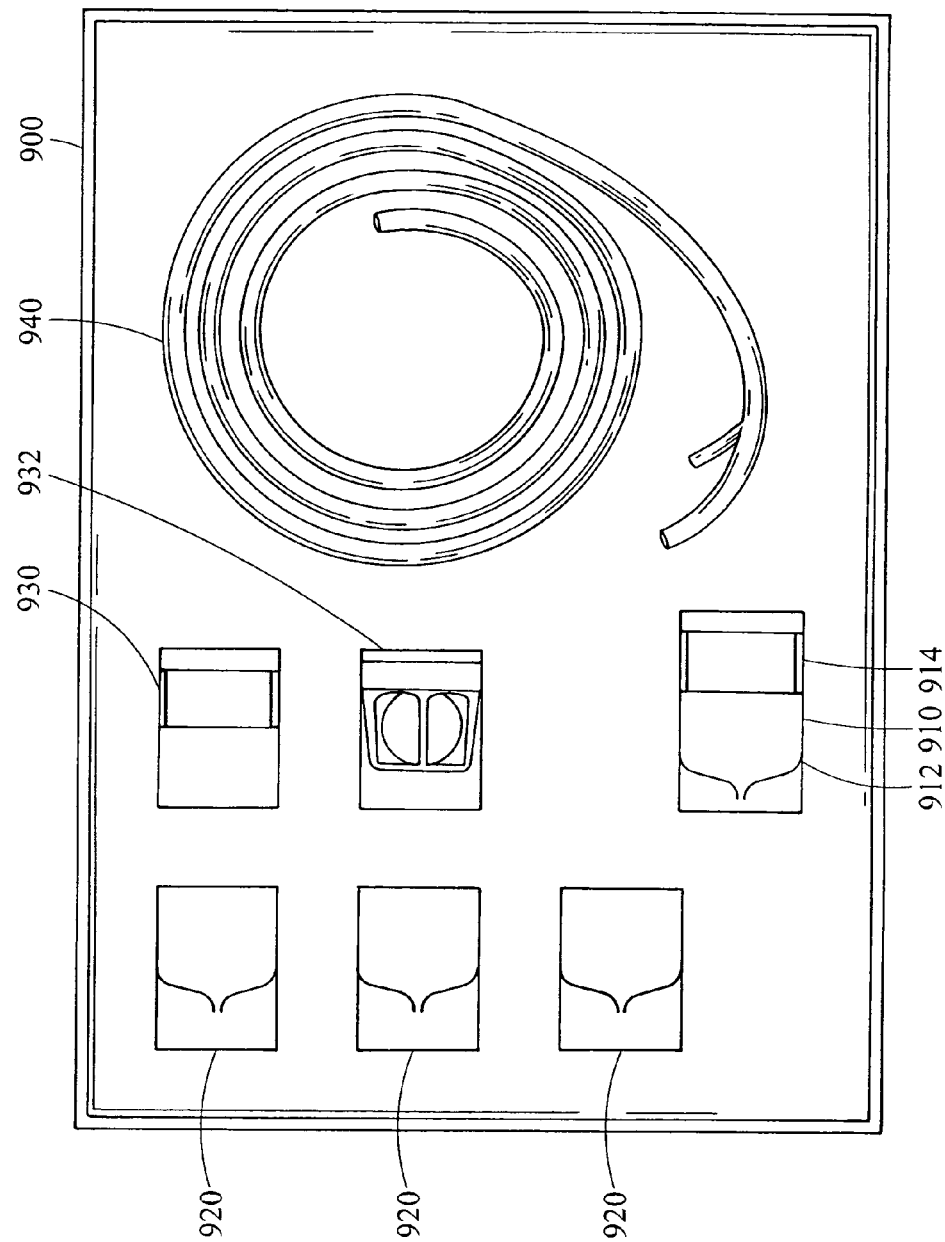
FIG. 6 is a schematic illustrating a kit according to one embodiment of the invention.

FIG. 6 illustrates a kit according to one embodiment of the invention. The kit 900 comprises a plurality of venous valve interfaces 920, a first flow-modifying device 930, a second flow-modifying device 932 and an implantable medical device 910 comprising both an interface 912 and a flow-modifying device 914 fixedly disposed at a flow-modifying effective distance with respect to each other (not showed). The kit 900 also includes a delivery catheter 940 for intraluminal implantation of a venous valve interface 920, a flow-modifying device 930, 932 or the implantable medical device 910.

Methods

Figure 7A:
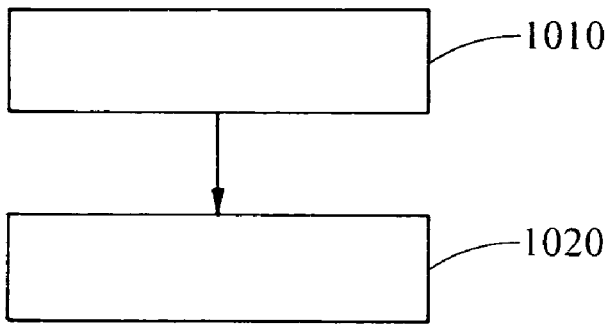
FIG. 7A and FIG. 7B are flowcharts illustrating methods of the invention.
Figure 7B:
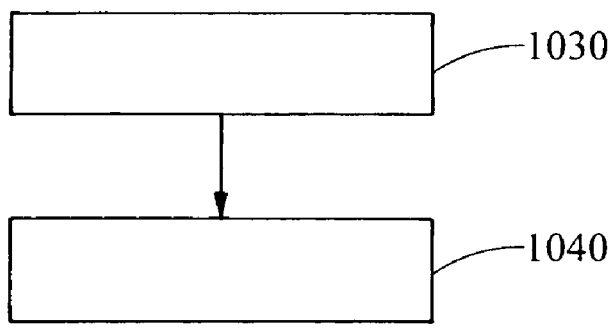

In one embodiment, the invention provides a method of modifying intraluminal fluid flow in a body vessel at an interface so as to preserve, enhance or promote a desired process at an interface. In one embodiment, illustrated in FIG. 7A, the process comprises the step of deploying an interface 1020 at a flow-modifying effective distance from a flow-modifying device that is previously positioned in a body vessel 1010. In another embodiment, illustrated in FIG. 7B, the process comprises the step of deploying a flow-modifying device 1040 at a flow-modifying effective distance from an interface that is previously positioned in a body vessel 1030.

Figure 8:
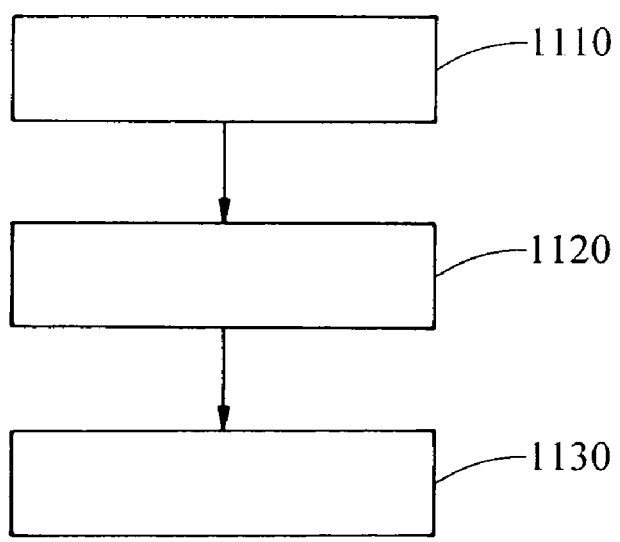
FIG. 8 is a flowchart illustrating another method of the invention.

In one embodiment, illustrated in FIG. 8, the invention provides a method of treating a patient comprising the acts of providing a first interface 1110, delivering the interface to a first point of treatment 1120, providing a flow-modifying device to a second point of treatment 1130, wherein the second point of treatment is spaced from the first point of treatment by a flow-modifying effective distance. In one embodiment, the flow-modifying device and the interface are operatively connected in a single implantable medical device and are delivered together to a single point of treatment (i.e., the first point of treatment and second point of treatment are substantially the same point). In one embodiment, multiple interfaces, or multiple flow-modifying devices, or any combination thereof, are delivered to multiple point of treatments.

The methods of the invention can be used to treat a variety of medical conditions. For example, one embodiment provides a method of treating a venous valve related condition, which refers to any condition presenting symptoms consistent with impaired venous valve function. One example of a venous valve related condition is venous valve insufficiency. Also provided are methods of treating medical conditions presenting symptoms consistent with impaired gastrointestinal, as well as urinary tract or biliary, function.

The acts of methods of the present invention can be done in any order, and can have other intervening steps or acts unless otherwise indicated.

It is intended that the foregoing detailed description be regarded as illustrative rather than limiting. The following claims, including all equivalents, that are intended to define the spirit and scope of this invention. Therefore, the embodiment of any figure and features thereof may be combined with the embodiments depicted in other figures. Other features known in the art and not inconsistent with the structure and function of the present invention may be added to the embodiments.

The recitations of "embodiments," "one embodiment," "some embodiments," "other embodiments," "illustrative embodiments," "selected embodiments," "certain embodiments," and "another embodiment" herein are synonymous. All of these recitations refer to illustrative embodiments and are not exclusive of each other or of other embodiments not recited herein. Accordingly, the invention also provides embodiments that comprise combinations of one or more of the illustrative embodiments described above. The invention also contemplates systems, methods and kits comprising, consisting of and consisting essentially of the elements and embodiments disclosed herein.

All references cited herein are hereby incorporated into this disclosure in their entirety.

We claim:

1. A method of treating a venous valve related medical condition comprising:
    intraluminally implanting a prosthetic venous valve within a vein, the venous valve including a valve leaflet comprising a remodelable material attached to a radially expandable support frame; and
    implanting a flow-modifying device comprising a bioabsorbable material configured as an occluding device or implantable ring within 15 cm of the prosthetic venous valve, to substantially prevent fluid flow toward the heart through the prosthetic venous valve for a period of at least about 3 weeks after intraluminal implantation of the flow-modifying device in the vein, and thereafter to permit fluid flow through the prosthetic venous valve after absorption of a portion of the bioabsorbable material in the flow-modifying device.

2. The method of claim 1, where the flow-modifying device and the prosthetic venous valve are implanted in a human deep vein selected from the group consisting of: a popliteal vein, a femoral vein, a tibial vein and a peroneal vein.

3. The method of claim 2, where the flow-modifying device is intraluminally implanted at a distance of between 1 mm and 5 cm from the remodelable material attached to the prosthetic venous valve.

4. The method of claim 2, where the flow-modifying device is configured and positioned to divert fluid flow from the deep venous system to the superficial venous system prior to absorption of the bioabsorbable material.

5. The method of claim 1, where the remodelable material comprises SIS.

6. The method of claim 1, where the flow-modifying device is a bioabsorbable flow-reducing ring.

7. The method of claim 1 where the flow-modifying device is positioned to divert fluid flow from a deep venous system to a superficial venous system prior to absorption of the bioabsorbable material.

8. The method of claim 7, where the flow-modifying device further comprises a tubular housing member defining an interior passage, the tubular housing member enclosing the the occluding device or implantable ring and the venous valve each positioned within the interior passage.

9. The method of claim 8, where the valve leaflet of the venous valve is a first valve leaflet and the venous valve further comprises two or more additional valve leaflets defining a valve orifice in combination with the first valve leaflet; and where the distance from the flow-modifying device to the valve orifice is between 1 mm and 15 cm.

10. A method of treating a venous valve related medical condition comprising:
    intraluminally implanting a first prosthetic venous valve within a deep venous system vein and a second prosthetic venous valve within a perforator vein connecting the deep venous system vein and a superficial venous system vein, each venous valve including a valve leaflet comprising a remodelable material attached to a radially expandable support frame; and
    intraluminally implanting a flow-modifying device within said deep venous system vein, the flow-modifying device comprising a bioabsorbable material configured as an occluding device or implantable ring upstream from the first prosthetic venous valve, where the flow-modifying device temporarily reduces blood flow toward the heart through the first and second prosthetic venous valves for a period between about 3 weeks and 3 months after intraluminal implantation of the flow-modifying device, thereby diverting blood flow from the deep venous system to other perforator veins prior to absorption of the bioabsorbable material for remodeling of each valve leaflet remodelable material, and thereafter, after absorption of the bioabsorbable material, blood flow is restored through the first and second prosthetic venous valves to a state similar to blood flow before intraluminal implantation of the flow-modifying device.

11. The method of claim 10, where the deep venous system vein is of a human, and the deep venous system vein is selected from the group consisting of: a popliteal vein, a femoral vein, a tibial vein and a peroneal vein.

12. The method of claim 11, where the flow-modifying device is a bioabsorbable flow-reducing ring, and is intraluminally implanted at a distance of between 1 mm and 5 cm from each of the first and second prosthetic venous valves.

13. A method of treating a venous valve related medical condition comprising: intraluminally implanting a prosthetic venous valve within a vein, the venous valve including a valve leaflet comprising a remodelable material attached to a radially expandable support frame; and implanting a flow-modifying device comprising a bioabsorbable material configured as an occluding device or implantable ring toward the heart from the prosthetic venous valve, the implanted flow modifying device being configured to substantially prevent blood flow toward the heart through the prosthetic venous valve for a period of at least about 3 weeks after intraluminal implantation of the flow-modifying device in the vein, and thereafter to permit fluid flow through the prosthetic venous valve after absorption of a portion of the bioabsorbable material in the flow-modifying device.

* * * * *

UNITED STATES PATENT AND TRADEMARK OFFICE
CERTIFICATE OF CORRECTION

PATENT NO. : 7,449,027 B2  Page 1 of 1
APPLICATION NO. : 11/093401
DATED : November 11, 2008
INVENTOR(S) : James B. Hunt et al.

It is certified that error appears in the above-identified patent and that said Letters Patent is hereby corrected as shown below:

On the Title Page

Page 2, in column 2, line 37, under "OTHER PUBLICATIONS", after "findings after" delete "in vivo" and substitute --*in vivo*-- (italics) in its place.

In the Claims

In column 26, claim 7, line 1, immediately after "claim 1" insert --,-- (comma).

In column 26, claim 8, line 7, after "member enclosing" delete "the" (second occurrence).

Signed and Sealed this

Twenty-sixth Day of May, 2009

JOHN DOLL
*Acting Director of the United States Patent and Trademark Office*